US007968281B2

(12) United States Patent
Nakamura et al.

(10) Patent No.: US 7,968,281 B2
(45) Date of Patent: Jun. 28, 2011

(54) METHODS OF MODULATING SMYD3 FOR TREATMENT OF CANCER

(75) Inventors: Yusuke Nakamura, Bunkyo-ku (JP);
Yoichi Furukawa, Bunkyo-ku (JP);
Ryuji Hamamoto, Bunkyo-ku (JP);
Shuichi Nakatsuru, Kawasaki (JP)

(73) Assignee: Oncotherapy Science, Inc., Kanagawa (JP)

( * ) Notice: Subject to any disclaimer, the term of this patent is extended or adjusted under 35 U.S.C. 154(b) by 80 days.

(21) Appl. No.: 11/912,860

(22) PCT Filed: Jun. 23, 2006

(86) PCT No.: PCT/JP2006/313038
§ 371 (c)(1),
(2), (4) Date: Dec. 23, 2008

(87) PCT Pub. No.: WO2007/004526
PCT Pub. Date: Jan. 11, 2007

(65) Prior Publication Data
US 2009/0191181 A1 Jul. 30, 2009

Related U.S. Application Data

(60) Provisional application No. 60/695,957, filed on Jul. 1, 2005.

(51) Int. Cl.
*C12Q 1/00* (2006.01)
*G01N 33/53* (2006.01)
(52) U.S. Cl. .......................................................... 435/4
(58) Field of Classification Search .................. None
See application file for complete search history.

(56) References Cited

U.S. PATENT DOCUMENTS

| 5,910,444 | A | * | 6/1999 | Masuta et al. ................. 435/419 |
| 2004/0235018 | A1 | | 11/2004 | Nakamura et al. |
| 2009/0035303 | A1 | | 2/2009 | Nakamura et al. |
| 2009/0142344 | A1 | | 6/2009 | Nakamura et al. |
| 2009/0175844 | A1 | | 7/2009 | Nakamura et al. |
| 2010/0184088 | A1 | | 7/2010 | Nakatsuru |
| 2010/0248240 | A1 | | 9/2010 | Nakamura et al. |

FOREIGN PATENT DOCUMENTS

| CN | 1 303 933 A | 7/2001 |
| EP | 0 390 530 A1 | 10/1990 |
| JP | 2004 264294 A | 9/2004 |
| WO | WO 00/17355 | 3/2000 |
| WO | WO 00/44900 | 8/2000 |
| WO | WO 02/059377 | 8/2002 |
| WO | WO 02/090578 | 11/2002 |
| WO | WO 02/092002 A2 | 11/2002 |
| WO | WO 03/010180 | 2/2003 |
| WO | WO 03/027143 A2 | 4/2003 |
| WO | WO03027143 | * 4/2003 |
| WO | WO 2004/076623 A2 | 9/2004 |
| WO | WO 2005/071102 A2 | 8/2005 |
| WO | WO 2008/152816 | 12/2008 |

OTHER PUBLICATIONS

Hamamoto et al, Nature Cell Biology, vol. 6, p. 731-740, 2004.*
Vandel et al, Mol & Cell Bio, 21:6484-6494, 2001.*
Hamamoto et al Nat Cell Bio, 6: 731-740, 2004.*
Sequence search result (Nakamura-Hamamoto)., 2010.*
Hamamoto, R., et al., "SMYD3 encodes a histone methyltransferase involved in the proliferation of cancer cells," Nature Cell Biology, vol. 6(8), pp. 731-740 (Jul. 4, 2004).
Database Geneseq [Online], "Human muscle BOP protein 41," EBI Accession No. GSP:AAG66728, abstract, Database Accession No. AAG66728, abstract (Nov. 26, 2001).
Du et al. "Hypermethylation in Human Cancers of the *RIZ1* Tumor Suppressor Gene, a Member of a Histone/Protein Methyltransferase Superfamily," Nov. 15, 2001, Cancer Res., 61(22): 8094-8099.
Echeverri et al., "siRNA Design: It's All the Algorithm," Oct. 3, 2004, Ambion TechNotes 11 (http:/www.ambion.com/techlib/tn/113/14.html).
Database NCBI, [Online] "*Homo sapiens* cDNA: FLJ21080 fls, clone CAS02449" EMBL Accession No. AK024733: Sep. 29, 2000.
Database NCBI, [Online] "AL557360 *Homo sapiens* T Cells (Jurkat Cell Line) *Homo sapiens* cDNA clone CS0DH004YB15 5-Prime, mRNA," EMBL Accession No. AL557360: Feb. 11, 2001.
Firestein et al., "Set Domain-Dependent Regulation of Transcriptional Silencing and Growth Control by SUV39H1, a Mammalian Ortholog of *Drosophila* Su(var)3-9," Jul. 2000, Mol. Cell Biol., 20(13): 4900-4909.
Fu T.B., et al., "The RNAs of hepatitis delta virus are copied by RNA polymerase II in nuclear homogenates," Dec. 1993, J. Virol., 67(12); 6965-6972.
Database NCBI, [Online], "*Homo sapiens* SET and MYND domain containing 3, mRNA (cDNA clone MGC:32757 Image:4334047), complete cds," GenBank Accession No. BC031010, Jun. 13, 2002.
Database Genecards [Online] Accession No. GC01M242239: Jan. 1, 2004. Hamamato et al., Proceedings/Annual Meeting of the American Association for Cancer Research/ Annual Meeting of the American Society of Clinical Oncology. American Association for Cancer Research. Meeting (43): 13-13: Mar. 1, 2002.
Hamamoto et al., "Enhanced SMYD3 expression is essential for the growth of breast cancer cells," Feb. 2006, Cancer Sci. 97(2): 113-118.
Hammato et al., 2001, Jpn. J. Cancer Res. (proceedings Sixtieth Annual Meeting of the Japanese Cancer Association), 92(Supplement): 117(208).
Kato et al., 2002, Jpn. J. Cancer Res. (proceedings Sixty-First Annual Meeting of the Japanese Cancer Association), 93(Supplement): 78(2033).
Luking et al., "The protein family of RNA helicases," 1998, Crit. Rev. Biochem Mol. Biol., 33(4): 259-296.
Nakajima et al., "RNA helicase A mediates association of CBP with RNA polymerase II," Sep. 19,1997, Cell, 90(6), 1107-1112.
Nozaki et al., 2004, The American Association For Cancer Research/ AACR; 45: 213(#934).

(Continued)

*Primary Examiner* — Misook Yu
*Assistant Examiner* — Lei Yao
(74) *Attorney, Agent, or Firm* — Kilpatrick Townsend & Stockton LLP

(57) ABSTRACT

The present invention features a method for determining the methyltransferase activity of a polypeptide and screening for modulators of methyltransferase activity, more particularly for modulators of the methylation of retinoblastoma by SMYD3. The invention further provides a method or pharmaceutical composition for prevention or treating of colorectal cancer, hepatocellular carcinoma, bladder cancer and/or breast cancer using a modulator so identified. N-terminal truncated forms of SMYD3 (alias ZNFN3A1) have higher methylating activity. Lys 824 is a preferred methylation site on the RB1 protein for SMYD3.

3 Claims, 16 Drawing Sheets

OTHER PUBLICATIONS

Okabe et al., "Genome-wide Analysis of Gene Expression in Human Hepatocellular Carcinomas Using cDNA Microarray: Identification of Genes Involved in Viral Carcinogenesis and Tumor Progression," Mar. 1, 2001, Cancer Res.,61(5): 2129-2137.

Rea et al., "Regulation of chromatin structure by site-specific histone H3 methyltransferases," Aug. 10, 2000, 406(6796): 593-599.

Rozoviskaia et al., "Self-association of the SET domains of human ALL-1 and of *Drosophila* TRITHORAX and ASH1 Proteins," Jan. 20, 2000, Oncogene, 19(3): 351-357.

Shibuya et al., "Differential roles of vascular endothelial growth factor receptor-1 and receptor-2 in angiogenesis," Sep. 30, 2006, J. Biochem. Mol. Biol., 39(5): 469-478.

Stockand et al., "*S*-Adenosyl-L-homocysteine Hydrolase Regulates Aldosterone-induced $Na^+$ Transport," Feb. 5, 1999, J. Biol. Chem., 274(6): 3842-3850.

Strahl et al., "Methylation of histone H3 at lysine 4 is highly conserved and correlates with transcriptionally active nuclei in *Tetrahymena*," Dec. 21, 1999, Proc. Natl. Acad. Sci. U.S.A., 96(26): 14967-14972.

Strausberg et al., "Generation and initial analysis of more than 15,000 full-length human and mouse cDNA sequences," Dec. 24, 2002, Proc. Natl. Acad. Sci. U.S.A., 99(26): 16899-16903.

Tsuge et al., "A variable number of tandem repeats polymorphism in an E2F-1 binding element in the 5' flanking region of SMYD3 is a risk factor for human cancers," Oct. 2005, Nat. Genet. 37(10): 1104-1107. Epub Sep. 11, 2005.

* cited by examiner

Continuation of Fig. 2
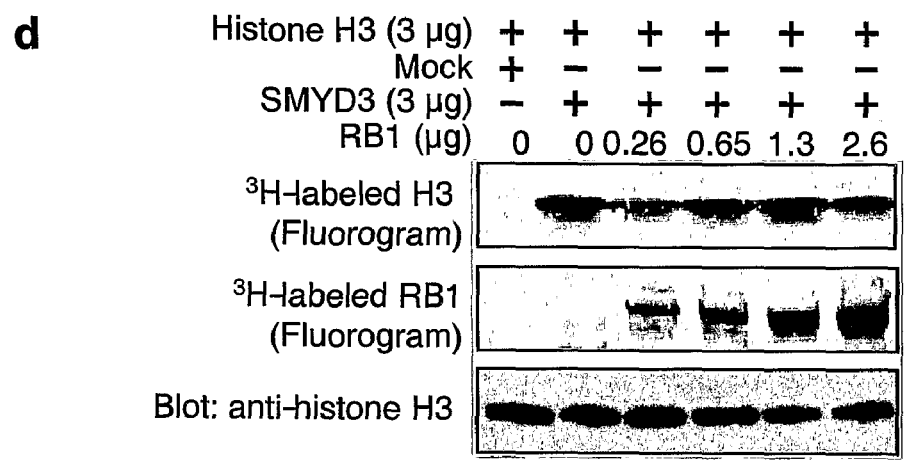
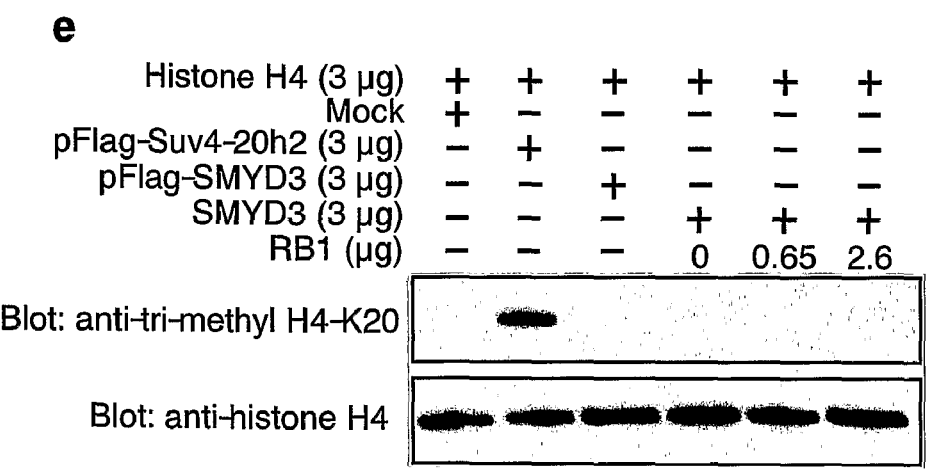

a b c

Continuation of Fig. 3
d 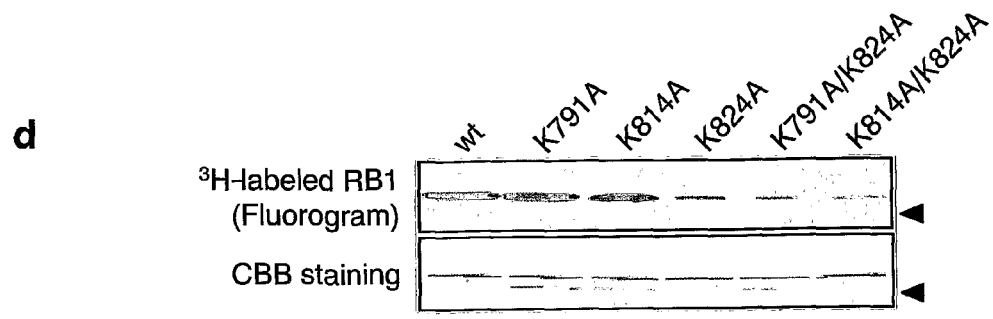
e 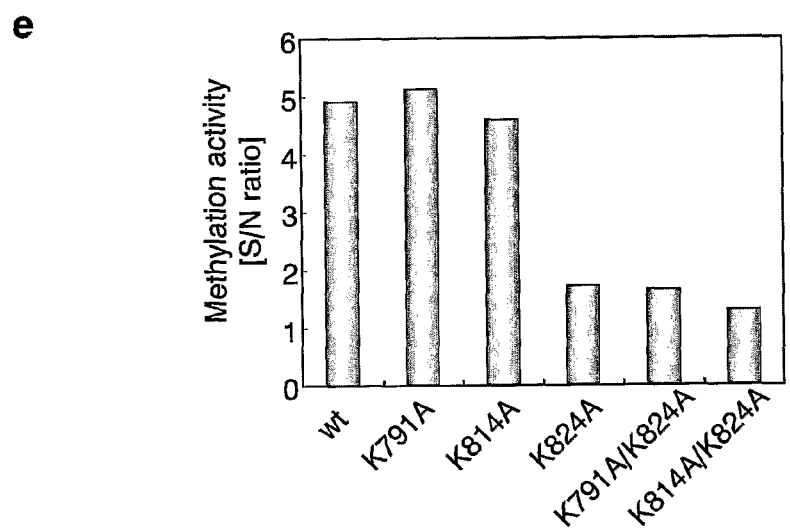
f 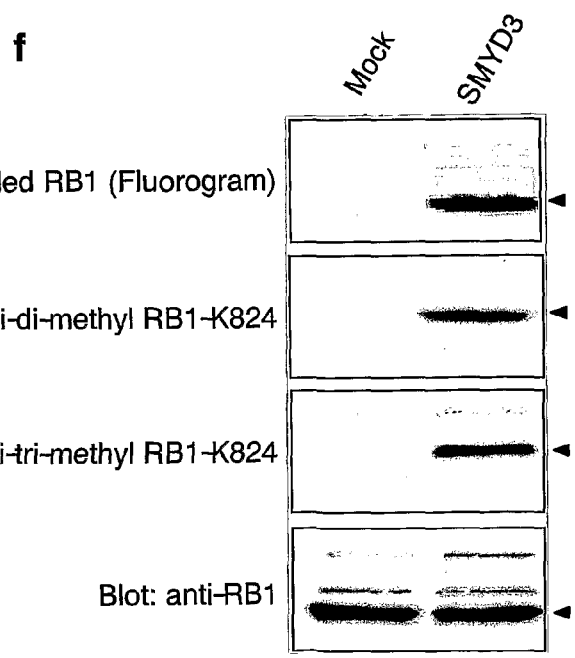

Continuation of Fig. 4
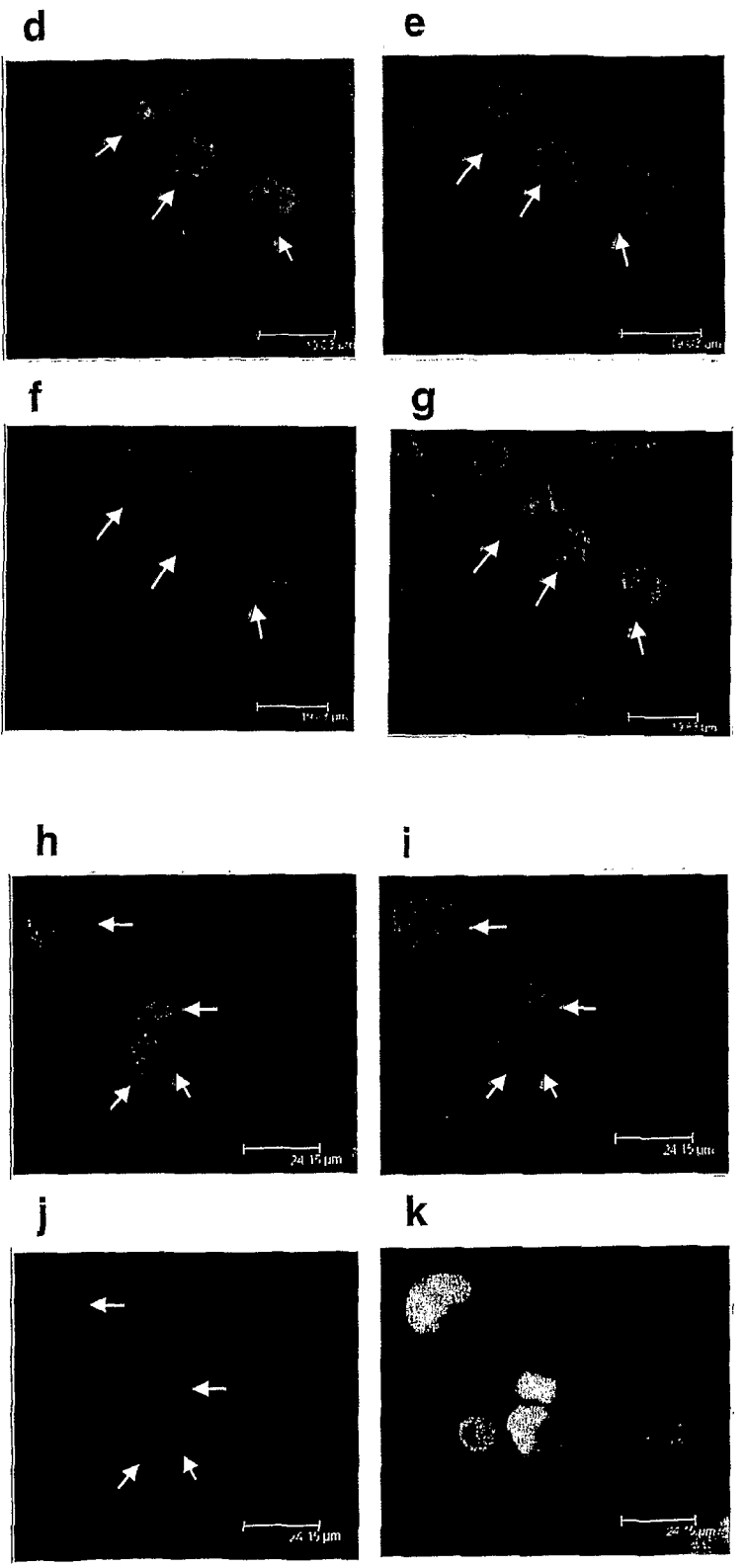

Continuation of Fig. 5
e
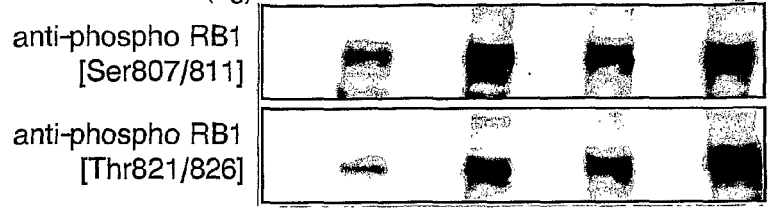
f
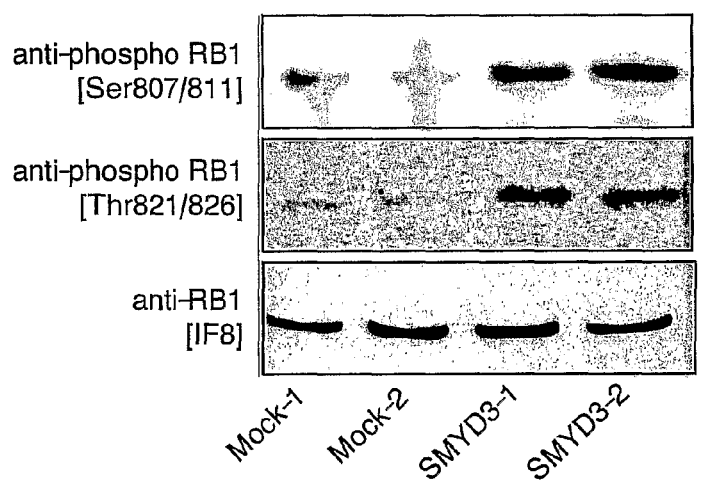
g
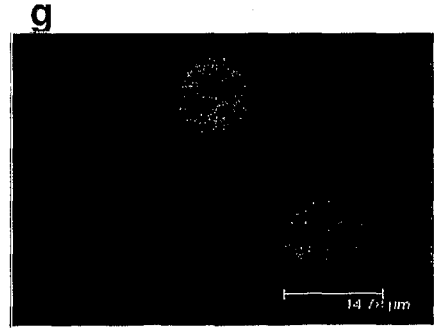
h
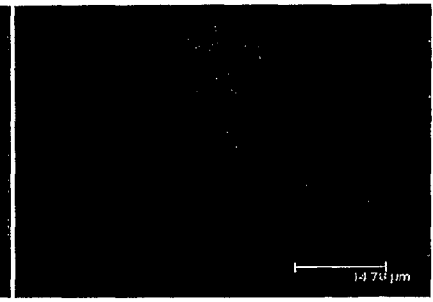
i
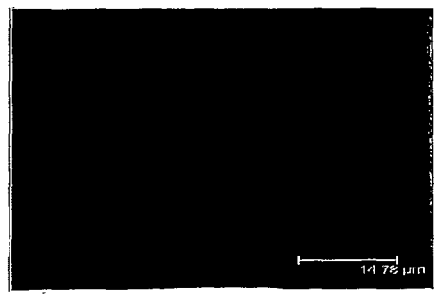
j
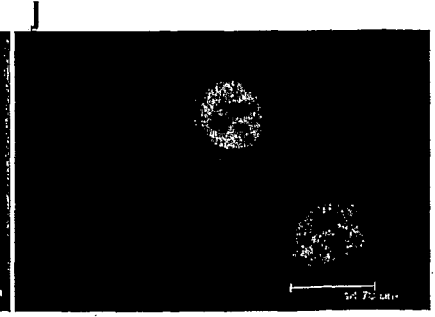

a b a b c

SEQUENCE LISTING

```
<160> NUMBER OF SEQ ID NOS: 38

<210> SEQ ID NO 1
<211> LENGTH: 1622
<212> TYPE: DNA
<213> ORGANISM: Homo sapiens
<220> FEATURE:
<223> OTHER INFORMATION: SET and MYND domain containing 3 (SMYD3), zinc
      finger protein, subfamily 3A (MYND domain containing) 1 (ZNFN3A1),
      zinc finger MYND domain-containing protein 1 (ZMYND1), histone
      H3-lysine 4-specific methyltransferase cDNA
<221> NAME/KEY: CDS
<222> LOCATION: (96)...(1382)
<223> OTHER INFORMATION: SMYD3

<400> SEQUENCE: 1
gtgcgcgcag ggcgcaggcg cgcgggtccc ggcagcccgt gagacgcccg ctgctggacg      60
cgggtagccg tctgaggtgc cggagctgcg ggagg atg gag ccg ctg aag gtg      113
                                      Met Glu Pro Leu Lys Val
                                        1               5 gaa aag ttc gca acc gcc aac agg gga aac ggg ctg cgc gcc gtg acc      161
Glu Lys Phe Ala Thr Ala Asn Arg Gly Asn Gly Leu Arg Ala Val Thr
              10                  15                  20 ccg ctg cgc ccc gga gag cta ctc ttc cgc tcg gat ccc ttg gcg tac      209
Pro Leu Arg Pro Gly Glu Leu Leu Phe Arg Ser Asp Pro Leu Ala Tyr
          25                  30                  35 acg gtg tgc aag ggg agt cgt ggc gtc gtc tgc gac cgc tgc ctt ctc      257
Thr Val Cys Lys Gly Ser Arg Gly Val Val Cys Asp Arg Cys Leu Leu
     40                  45                  50 ggg aag gaa aag ctg atg cga tgc tct cag tgc cgc gtc gcc aaa tac      305
Gly Lys Glu Lys Leu Met Arg Cys Ser Gln Cys Arg Val Ala Lys Tyr
 55                  60                  65                  70 tgt agt gct aag tgt cag aaa aaa gct tgg cca gac cac aag cgg gaa      353
Cys Ser Ala Lys Cys Gln Lys Lys Ala Trp Pro Asp His Lys Arg Glu
                 75                  80                  85 tgc aaa tgc ctt aaa agc tgc aaa ccc aga tat cct cca gac tcc gtt      401
Cys Lys Cys Leu Lys Ser Cys Lys Pro Arg Tyr Pro Pro Asp Ser Val
             90                  95                 100 cga ctt ctt ggc aga gtt gtc ttc aaa ctt atg gat gga gca cct tca      449
Arg Leu Leu Gly Arg Val Val Phe Lys Leu Met Asp Gly Ala Pro Ser
         105                 110                 115 gaa tca gag aag ctt tac tca ttt tat gat ctg gag tca aat att aac      497
Glu Ser Glu Lys Leu Tyr Ser Phe Tyr Asp Leu Glu Ser Asn Ile Asn
 120                 125                 130 aaa ctg act gaa gat aag aaa gag ggc ctc agg caa ctc gta atg aca      545
Lys Leu Thr Glu Asp Lys Lys Glu Gly Leu Arg Gln Leu Val Met Thr
135                 140                 145                 150 ttt caa cat ttc atg aga gaa gaa ata cag gat gcc tct cag ctg cca      593
Phe Gln His Phe Met Arg Glu Glu Ile Gln Asp Ala Ser Gln Leu Pro
                 155                 160                 165 cct gcc ttt gac ctt ttt gaa gcc ttt gca aaa gtg atc tgc aac tct      641
```

```
       Pro Ala Phe Asp Leu Phe Glu Ala Phe Ala Lys Val Ile Cys Asn Ser
                       170                 175                 180 ttc acc atc tgt aat gcg gag atg cag gaa gtt ggt gtt ggc cta tat       689
Phe Thr Ile Cys Asn Ala Glu Met Gln Glu Val Gly Val Gly Leu Tyr
            185                 190                 195 ccc agt atc tct ttg ctc aat cac agc tgt gac ccc aac tgt tcg att       737
Pro Ser Ile Ser Leu Leu Asn His Ser Cys Asp Pro Asn Cys Ser Ile
        200                 205                 210 gtg ttc aat ggg ccc cac ctc tta ctg cga gca gtc cga gac atc gag       785
Val Phe Asn Gly Pro His Leu Leu Leu Arg Ala Val Arg Asp Ile Glu
215                 220                 225                 230 gtg gga gag gag ctc acc atc tgc tac ctg gat atg ctg atg acc agt       833
Val Gly Glu Glu Leu Thr Ile Cys Tyr Leu Asp Met Leu Met Thr Ser
                235                 240                 245 gag gag cgc cgg aag cag ctg agg gac cag tac tgc ttt gaa tgt gac       881
Glu Glu Arg Arg Lys Gln Leu Arg Asp Gln Tyr Cys Phe Glu Cys Asp
            250                 255                 260 tgt ttc cgt tgc caa acc cag gac aag gat gct gat atg cta act ggt       929
Cys Phe Arg Cys Gln Thr Gln Asp Lys Asp Ala Asp Met Leu Thr Gly
        265                 270                 275 gat gag caa gta tgg aag gaa gtt caa gaa tcc ctg aaa aaa att gaa       977
Asp Glu Gln Val Trp Lys Glu Val Gln Glu Ser Leu Lys Lys Ile Glu
280                 285                 290 gaa ctg aag gca cac tgg aag tgg gag cag gtt ctg gcc atg tgc cag      1025
Glu Leu Lys Ala His Trp Lys Trp Glu Gln Val Leu Ala Met Cys Gln
295                 300                 305                 310 gca atc ata agc agc aat tct gaa cgg ctt ccc gat atc aac atc tac      1073
Ala Ile Ile Ser Ser Asn Ser Glu Arg Leu Pro Asp Ile Asn Ile Tyr
                315                 320                 325 cag ctg aag gtg ctc gac tgc gcc atg gat gcc tgc atc aac ctc ggc      1121
Gln Leu Lys Val Leu Asp Cys Ala Met Asp Ala Cys Ile Asn Leu Gly
            330                 335                 340 ctg ttg gag gaa gcc ttg ttc tat ggt act cgg acc atg gag cca tac      1169
Leu Leu Glu Glu Ala Leu Phe Tyr Gly Thr Arg Thr Met Glu Pro Tyr
        345                 350                 355 agg att ttt ttc cca gga agc cat ccc gtc aga ggg gtt caa gtg atg      1217
Arg Ile Phe Phe Pro Gly Ser His Pro Val Arg Gly Val Gln Val Met
360                 365                 370 aaa gtt ggc aaa ctg cag cta cat caa ggc atg ttt ccc caa gca atg      1265
Lys Val Gly Lys Leu Gln Leu His Gln Gly Met Phe Pro Gln Ala Met
375                 380                 385                 390 aag aat ctg aga ctg gct ttt gat att atg aga gtg aca cat ggc aga      1313
Lys Asn Leu Arg Leu Ala Phe Asp Ile Met Arg Val Thr His Gly Arg
                395                 400                 405 gaa cac agc ctg att gaa gat ttg att cta ctt tta gaa gaa tgc gac      1361
Glu His Ser Leu Ile Glu Asp Leu Ile Leu Leu Glu Glu Cys Asp
            410                 415                 420 gcc aac atc aga gca tcc taa gggaacgcag tcagagggaa atacggcgtg         1412
Ala Asn Ile Arg Ala Ser
                425 tgtctttgtt gaatgcctta ttgaggtcac acactctatg ctttgttagc tgtgtgaacc    1472 tctcctattg gaaattctgt tccgtgtttg tgtaggtaaa taaaggcaga catggtttgc    1532 aaaccacaag aatcattagt tgtagagaag cacgattata ataaattcaa acatttggt    1592 tgaggatgcc aaaaaaaaaa aaaaaaaaa                                      1622

<210> SEQ ID NO 2
<211> LENGTH: 428
<212> TYPE: PRT
<213> ORGANISM: Homo sapiens
```

```
<220> FEATURE:
<223> OTHER INFORMATION: SET and MYND domain containing 3 (SMYD3), zinc
      finger protein, subfamily 3A (MYND domain containing) 1 (ZNFN3A1),
      zinc finger MYND domain-containing protein 1 (ZMYND1), histone
      H3-lysine 4-specific methyltransferase

<400> SEQUENCE: 2

Met Glu Pro Leu Lys Val Glu Lys Phe Ala Thr Ala Asn Arg Gly Asn
 1               5                  10                  15

Gly Leu Arg Ala Val Thr Pro Leu Arg Pro Gly Glu Leu Leu Phe Arg
                20                  25                  30

Ser Asp Pro Leu Ala Tyr Thr Val Cys Lys Gly Ser Arg Gly Val Val
            35                  40                  45

Cys Asp Arg Cys Leu Leu Gly Lys Glu Lys Leu Met Arg Cys Ser Gln
 50                  55                  60

Cys Arg Val Ala Lys Tyr Cys Ser Ala Lys Cys Gln Lys Lys Ala Trp
 65                  70                  75                  80

Pro Asp His Lys Arg Glu Cys Lys Cys Leu Lys Ser Cys Lys Pro Arg
                85                  90                  95

Tyr Pro Pro Asp Ser Val Arg Leu Leu Gly Arg Val Val Phe Lys Leu
            100                 105                 110

Met Asp Gly Ala Pro Ser Glu Ser Glu Lys Leu Tyr Ser Phe Tyr Asp
        115                 120                 125

Leu Glu Ser Asn Ile Asn Lys Leu Thr Glu Asp Lys Lys Glu Gly Leu
130                 135                 140

Arg Gln Leu Val Met Thr Phe Gln His Phe Met Arg Glu Glu Ile Gln
145                 150                 155                 160

Asp Ala Ser Gln Leu Pro Pro Ala Phe Asp Leu Phe Glu Ala Phe Ala
                165                 170                 175

Lys Val Ile Cys Asn Ser Phe Thr Ile Cys Asn Ala Glu Met Gln Glu
            180                 185                 190

Val Gly Val Gly Leu Tyr Pro Ser Ile Ser Leu Leu Asn His Ser Cys
        195                 200                 205

Asp Pro Asn Cys Ser Ile Val Phe Asn Gly Pro His Leu Leu Leu Arg
210                 215                 220

Ala Val Arg Asp Ile Glu Val Gly Glu Glu Leu Thr Ile Cys Tyr Leu
225                 230                 235                 240

Asp Met Leu Met Thr Ser Glu Glu Arg Arg Lys Gln Leu Arg Asp Gln
                245                 250                 255

Tyr Cys Phe Glu Cys Asp Cys Phe Arg Cys Gln Thr Gly Asp Lys Asp
            260                 265                 270

Ala Asp Met Leu Thr Gly Asp Glu Gln Val Trp Lys Glu Val Gln Glu
        275                 280                 285

Ser Leu Lys Lys Ile Glu Glu Leu Lys Ala His Trp Lys Trp Glu Gln
290                 295                 300

Val Leu Ala Met Cys Gln Ala Ile Ile Ser Ser Asn Ser Glu Arg Leu
305                 310                 315                 320

Pro Asp Ile Asn Ile Tyr Gln Leu Lys Val Leu Asp Cys Ala Met Asp
                325                 330                 335

Ala Cys Ile Asn Leu Gly Leu Leu Glu Glu Ala Leu Phe Tyr Gly Thr
            340                 345                 350

Arg Thr Met Glu Pro Tyr Arg Ile Phe Phe Pro Gly Ser His Pro Val
        355                 360                 365

Arg Gly Val Gln Val Met Lys Val Gly Lys Leu Gln Leu His Gln Gly
370                 375                 380
```

```
Met Phe Pro Gln Ala Met Lys Asn Leu Arg Leu Ala Phe Asp Ile Met
385                 390                 395                 400

Arg Val Thr His Gly Arg Glu His Ser Leu Ile Glu Asp Leu Ile Leu
            405                 410                 415

Leu Leu Glu Glu Cys Asp Ala Asn Ile Arg Ala Ser
        420                 425

<210> SEQ ID NO 3
<211> LENGTH: 4740
<212> TYPE: DNA
<213> ORGANISM: Homo sapiens
<220> FEATURE:
<223> OTHER INFORMATION: retinoblastoma 1 protein (RB1), retinoblastoma
      susceptibility protein, OSRC. p105-Rb, pRb, RB
<221> NAME/KEY: CDS
<222> LOCATION: (139)...(2925)
<223> OTHER INFORMATION: RB1

<400> SEQUENCE: 3
ttccggtttt tctcagggga cgttgaaatt atttttgtaa cgggagtcgg gagaggacgg      60
ggcgtgcccc gcgtgcgcgc gcgtcgtcct ccccggcgct cctccacagc tcgctggctc    120
ccgccgcgga aaggcgtc atg ccg ccc aaa acc ccc cga aaa acg gcc gcc       171
                    Met Pro Pro Lys Thr Pro Arg Lys Thr Ala Ala
                     1               5                  10 acc gcc gcc gct gcc gcc gcg gaa ccc ccg gca ccg ccg ccg ccc           219
Thr Ala Ala Ala Ala Ala Ala Glu Pro Pro Ala Pro Pro Pro Pro
                 15                  20                  25 cct cct gag gag gac cca gag cag gac agc ggc ccg gag gac ctg cct       267
Pro Pro Glu Glu Asp Pro Glu Gln Asp Ser Gly Pro Glu Asp Leu Pro
            30                  35                  40 ctc gtc agg ctt gag ttt gaa gaa aca gaa gaa cct gat ttt act gca       315
Leu Val Arg Leu Glu Phe Glu Glu Thr Glu Glu Pro Asp Phe Thr Ala
        45                  50                  55 tta tgt cag aaa tta aag ata cca gat cat gtc aga gag aga gct tgg       363
Leu Cys Gln Lys Leu Lys Ile Pro Asp His Val Arg Glu Arg Ala Trp
 60                  65                  70                  75 tta act tgg gag aaa gtt tca tct gtg gat gga gta ttg gga ggt tat       411
Leu Thr Trp Glu Lys Val Ser Ser Val Asp Gly Val Leu Gly Gly Tyr
                 80                  85                  90 att caa aag aaa aag gaa ctg tgg gga atc tgt atc ttt att gca cga       459
Ile Gln Lys Lys Lys Glu Leu Trp Gly Ile Cys Ile Phe Ile Ala Arg
             95                 100                 105 gtt gac cta gat gag atg tcg ttc act tta ctg agc tac aga aaa aca       507
Val Asp Leu Asp Glu Met Ser Phe Thr Leu Leu Ser Tyr Arg Lys Thr
        110                 115                 120 tac gaa atc agt gtc cat aaa ttc ttt aac tta cta aaa gaa att gat       555
Tyr Glu Ile Ser Val His Lys Phe Phe Asn Leu Leu Lys Glu Ile Asp
    125                 130                 135 acc agt acc aaa gtt gat aat gct atg tca aga ctg ttg aag aag tat       603
Thr Ser Thr Lys Val Asp Asn Ala Met Ser Arg Leu Leu Lys Lys Tyr
140                 145                 150                 155 gat gta ttg ttt gca ctc ttc agc aaa ttg gaa agg aca tgt gaa ctt       651
Asp Val Leu Phe Ala Leu Phe Ser Lys Leu Glu Arg Thr Cys Glu Leu
                160                 165                 170 ata tat ttg aca caa ccc agc agt tcg ata tct act gaa ata aat tct       699
Ile Tyr Leu Thr Gln Pro Ser Ser Ser Ile Ser Thr Glu Ile Asn Ser
            175                 180                 185 gca ttg gtg cta aaa gtt tct tgg atc aca ttt tta tta gct aaa ggg       747
Ala Leu Val Leu Lys Val Ser Trp Ile Thr Phe Leu Leu Ala Lys Gly
        190                 195                 200 gaa gta tta caa atg gaa gat gat ctg gtg att tca ttt cag tta atg       795
```

| | | | | | | | | | | | | | |
|---|---|---|---|---|---|---|---|---|---|---|---|---|---|
| Glu | Val | Leu | Gln | Met | Glu | Asp | Asp | Leu | Val | Ile | Ser | Phe | Gln | Leu | Met |
| | 205 | | | | 210 | | | | 215 | | | | | |

```
cta tgt gtc ctt gac tat ttt att aaa ctc tca cct ccc atg ttg ctc     843
Leu Cys Val Leu Asp Tyr Phe Ile Lys Leu Ser Pro Pro Met Leu Leu
220                 225                 230                 235 aaa gaa cca tat aaa aca gct gtt ata ccc att aat gga tca cct cga     891
Lys Glu Pro Tyr Lys Thr Ala Val Ile Pro Ile Asn Gly Ser Pro Arg
                240                 245                 250 aca ccc agg cga ggt cag aac agg agt gca cgg ata gca aaa caa cta     939
Thr Pro Arg Arg Gly Gln Asn Arg Ser Ala Arg Ile Ala Lys Gln Leu
            255                 260                 265 gaa aat gat aca aga att att gaa gtt ctc tgt aaa gaa cat gaa tgt     987
Glu Asn Asp Thr Arg Ile Ile Glu Val Leu Cys Lys Glu His Glu Cys
        270                 275                 280 aat ata gat gag gtg aaa aat gtt tat ttc aaa aat ttt ata cct ttt    1035
Asn Ile Asp Glu Val Lys Asn Val Tyr Phe Lys Asn Phe Ile Pro Phe
    285                 290                 295 atg aat tct ctt gga ctt gta aca tct aat gga ctt cca gag gtt gaa    1083
Met Asn Ser Leu Gly Leu Val Thr Ser Asn Gly Leu Pro Glu Val Glu
300                 305                 310                 315 aat ctt tct aaa cga tac gaa gaa att tat ctt aaa aat aaa gat cta    1131
Asn Leu Ser Lys Arg Tyr Glu Glu Ile Tyr Leu Lys Asn Lys Asp Leu
                320                 325                 330 gat cga aga tta ttt ttg gat cat gat aaa act ctt cag act gat tct    1179
Asp Arg Arg Leu Phe Leu Asp His Asp Lys Thr Leu Gln Thr Asp Ser
            335                 340                 345 ata gac agt ttt gaa aca cag aga aca cca cga aaa agt aac ctt gat    1227
Ile Asp Ser Phe Glu Thr Gln Arg Thr Pro Arg Lys Ser Asn Leu Asp
        350                 355                 360 gaa gag gtg aat ata att cct cca cac act cca gtt agg act gtt atg    1275
Glu Glu Val Asn Ile Ile Pro Pro His Thr Pro Val Arg Thr Val Met
    365                 370                 375 aac act atc caa caa tta atg atg att tta aat tct gca agt gat caa    1323
Asn Thr Ile Gln Gln Leu Met Met Ile Leu Asn Ser Ala Ser Asp Gln
380                 385                 390                 395 cct tca gaa aat ctg att tcc tat ttt aac aac tgc aca gtg aat cca    1371
Pro Ser Glu Asn Leu Ile Ser Tyr Phe Asn Asn Cys Thr Val Asn Pro
                400                 405                 410 aaa gaa agt ata ctg aaa aga gtg aag gat ata gga tac atc ttt aaa    1419
Lys Glu Ser Ile Leu Lys Arg Val Lys Asp Ile Gly Tyr Ile Phe Lys
            415                 420                 425 gag aaa ttt gct aaa gct gtg gga cag ggt tgt gtc gaa att gga tca    1467
Glu Lys Phe Ala Lys Ala Val Gly Gln Gly Cys Val Glu Ile Gly Ser
        430                 435                 440 cag cga tac aaa ctt gga gtt cgc ttg tat tac cga gta atg gaa tcc    1515
Gln Arg Tyr Lys Leu Gly Val Arg Leu Tyr Tyr Arg Val Met Glu Ser
    445                 450                 455 atg ctt aaa tca gaa gaa gaa cga tta tcc att caa aat ttt agc aaa    1563
Met Leu Lys Ser Glu Glu Glu Arg Leu Ser Ile Gln Asn Phe Ser Lys
460                 465                 470                 475 ctt ctg aat gac aac att ttt cat atg tct tta ttg gcg tgc gct ctt    1611
Leu Leu Asn Asp Asn Ile Phe His Met Ser Leu Leu Ala Cys Ala Leu
                480                 485                 490 gag gtt gta atg gcc aca tat agc aga agt aca tct cag aat ctt gat    1659
Glu Val Val Met Ala Thr Tyr Ser Arg Ser Thr Ser Gln Asn Leu Asp
            495                 500                 505 tct gga aca gat ttg tct ttc cca tgg att ctg aat gtg ctt aat tta    1707
Ser Gly Thr Asp Leu Ser Phe Pro Trp Ile Leu Asn Val Leu Asn Leu
        510                 515                 520 aaa gcc ttt gat ttt tac aaa gtg atc gaa agt ttt atc aaa gca gaa    1755
```

```
                    Lys Ala Phe Asp Phe Tyr Lys Val Ile Glu Ser Phe Ile Lys Ala Glu
                        525                 530                 535 ggc aac ttg aca aga gaa atg ata aaa cat tta gaa cga tgt gaa cat       1803
Gly Asn Leu Thr Arg Glu Met Ile Lys His Leu Glu Arg Cys Glu His
540                 545                 550                 555 cga atc atg gaa tcc ctt gca tgg ctc tca gat tca cct tta ttt gat       1851
Arg Ile Met Glu Ser Leu Ala Trp Leu Ser Asp Ser Pro Leu Phe Asp
                560                 565                 570 ctt att aaa caa tca aag gac cga gaa gga cca act gat cac ctt gaa       1899
Leu Ile Lys Gln Ser Lys Asp Arg Glu Gly Pro Thr Asp His Leu Glu
            575                 580                 585 tct gct tgt cct ctt aat ctt cct ctc cag aat aat cac act gca gca       1947
Ser Ala Cys Pro Leu Asn Leu Pro Leu Gln Asn Asn His Thr Ala Ala
        590                 595                 600 gat atg tat ctt tct cct gta aga tct cca aag aaa aaa ggt tca act       1995
Asp Met Tyr Leu Ser Pro Val Arg Ser Pro Lys Lys Lys Gly Ser Thr
    605                 610                 615 acg cgt gta aat tct act gca aat gca gag aca caa gca acc tca gcc       2043
Thr Arg Val Asn Ser Thr Ala Asn Ala Glu Thr Gln Ala Thr Ser Ala
620                 625                 630                 635 ttc cag acc cag aag cca ttg aaa tct acc tct ctt tca ctg ttt tat       2091
Phe Gln Thr Gln Lys Pro Leu Lys Ser Thr Ser Leu Ser Leu Phe Tyr
                640                 645                 650 aaa aaa gtg tat cgg cta gcc tat ctc cgg cta aat aca ctt tgt gaa       2139
Lys Lys Val Tyr Arg Leu Ala Tyr Leu Arg Leu Asn Thr Leu Cys Glu
            655                 660                 665 cgc ctt ctg tct gag cac cca gaa tta gaa cat atc atc tgg acc ctt       2187
Arg Leu Leu Ser Glu His Pro Glu Leu Glu His Ile Ile Trp Thr Leu
        670                 675                 680 ttc cag cac acc ctg cag aat gag tat gaa ctc atg aga gac agg cat       2235
Phe Gln His Thr Leu Gln Asn Glu Tyr Glu Leu Met Arg Asp Arg His
    685                 690                 695 ttg gac caa att atg atg tgt tcc atg tat ggc ata tgc aaa gtg aag       2283
Leu Asp Gln Ile Met Met Cys Ser Met Tyr Gly Ile Cys Lys Val Lys
700                 705                 710                 715 aat ata gac ctt aaa ttc aaa atc att gta aca gca tac aag gat ctt       2331
Asn Ile Asp Leu Lys Phe Lys Ile Ile Val Thr Ala Tyr Lys Asp Leu
                720                 725                 730 cct cat gct gtt cag gag aca ttc aaa cgt gtt ttg atc aaa gaa gag       2379
Pro His Ala Val Gln Glu Thr Phe Lys Arg Val Leu Ile Lys Glu Glu
            735                 740                 745 gag tat gat tct att ata gta ttc tat aac tcg gtc ttc atg cag aga       2427
Glu Tyr Asp Ser Ile Ile Val Phe Tyr Asn Ser Val Phe Met Gln Arg
        750                 755                 760 ctg aaa aca aat att ttg cag tat gct tcc acc agg ccc cct acc ttg       2475
Leu Lys Thr Asn Ile Leu Gln Tyr Ala Ser Thr Arg Pro Pro Thr Leu
    765                 770                 775 tca cca ata cct cac att cct cga agc cct tac aag ttt cct agt tca       2523
Ser Pro Ile Pro His Ile Pro Arg Ser Pro Tyr Lys Phe Pro Ser Ser
780                 785                 790                 795 ccc tta cgg att cct gga ggg aac atc tat att tca ccc ctg aag agt       2571
Pro Leu Arg Ile Pro Gly Gly Asn Ile Tyr Ile Ser Pro Leu Lys Ser
                800                 805                 810 cca tat aaa att tca gaa ggt ctg cca aca cca aca aaa atg act cca       2619
Pro Tyr Lys Ile Ser Glu Gly Leu Pro Thr Pro Thr Lys Met Thr Pro
            815                 820                 825 aga tca aga atc tta gta tca att ggt gaa tca ttc ggg act tct gag       2667
Arg Ser Arg Ile Leu Val Ser Ile Gly Glu Ser Phe Gly Thr Ser Glu
        830                 835                 840 aag ttc cag aaa ata aat cag atg gta tgt aac agc gac cgt gtg ctc       2715
```

| | | |
|---|---|---|
| Lys Phe Gln Lys Ile Asn Gln Met Val Cys Asn Ser Asp Arg Val Leu<br>845              850                  855 | | |
| aaa aga agt gct gaa gga agc aac cct cct aaa cca ctg aaa aaa cta<br>Lys Arg Ser Ala Glu Gly Ser Asn Pro Pro Lys Pro Leu Lys Lys Leu<br>860              865                  870                  875 | | 2763 |
| cgc ttt gat att gaa gga tca gat gaa gca gat gga agt aaa cat ctc<br>Arg Phe Asp Ile Glu Gly Ser Asp Glu Ala Asp Gly Ser Lys His Leu<br>                  880                  885                  890 | | 2811 |
| cca gga gag tcc aaa ttt cag cag aaa ctg gca gaa atg act tct act<br>Pro Gly Glu Ser Lys Phe Gln Gln Lys Leu Ala Glu Met Thr Ser Thr<br>              895                  900                  905 | | 2859 |
| cga aca cga atg caa aag cag aaa atg aat gat agc atg gat acc tca<br>Arg Thr Arg Met Gln Lys Gln Lys Met Asn Asp Ser Met Asp Thr Ser<br>          910                  915                  920 | | 2907 |
| aac aag gaa gag aaa tga ggatctcagg accttggtgg acactgtgta<br>Asn Lys Glu Glu Lys<br>          925 | | 2955 |
| cacctctgga ttcattgtct ctcacagatg tgactgtata actttcccag gttctgttta | | 3015 |
| tggccacatt taatatcttc agctcttttt gtggatataa aatgtgcaga tgcaattgtt | | 3075 |
| tgggtgagtc ctaagccact tgaaatgtta gtcattgtta tttatacaag attgaaaatc | | 3135 |
| ttgtgtaaat cctgccattt aaaaagttgt agcagattgt ttcctcttcc aaagtaaaat | | 3195 |
| tgctgtgctt tatggatagt aagaatggcc ctagagtggg agtcctgata acccaggcct | | 3255 |
| gtctgactac tttgccttct tttgtagcat ataggtgatg tttgctcttg tttttattaa | | 3315 |
| tttatatgta tattttttta atttaacatg aacacccctta gaaatgtgt cctatctatc | | 3375 |
| ttccaaatgc aatttgattg actgcccatt caccaaaatt atcctgaact cttctgcaaa | | 3435 |
| aatggatatt attagaaatt agaaaaaaat tactaatttt acacattaga tttattttta | | 3495 |
| ctattggaat ctgatatact gtgtgcttgt tttataaaat tttgctttta attaaataaa | | 3555 |
| agctggaagc aaagtataac catatgatac tatcatacta ctgaaacaga tttcatacct | | 3615 |
| cagaatgtaa aagaacttac tgattatttt cttcatccaa cttatgtttt taaatgagga | | 3675 |
| ttattgatag tactcttggt ttttatacca ttcagatcac tgaatttata agtacccat | | 3735 |
| ctagtacttg aaaaagtaaa gtgttctgcc agatcttagg tatagaggac cctaacacag | | 3795 |
| tatatcccaa gtgcactttc taatgtttct gggtcctgaa gaattaagat acaaattaat | | 3855 |
| tttactccat aaacagactg ttaattatag gagccttaat ttttttttca tagagatttg | | 3915 |
| tctaattgca tctcaaaatt attctgccct ccttaatttg ggaaggtttg tgttttctct | | 3975 |
| ggaatggtac atgtcttcca tgtatctttt gaactggcaa ttgtctattt atcttttatt | | 4035 |
| ttttaagtc agtatggtct aacactggca tgttcaaagc cacattattt ctagtccaaa | | 4095 |
| attacaagta atcaagggtc attatgggtt aggcattaat gtttctatct gattttgtgc | | 4155 |
| aaaagcttca aattaaaaca gctgcattag aaaaagaggc gcttctcccc tcccctacac | | 4215 |
| ctaaaggtgt atttaaacta tcttgtgtga ttaacttatt tagagatgct gtaacttaaa | | 4275 |
| atagggata tttaaggtag cttcagctag cttttaggaa aatcactttg tctaactcag | | 4335 |
| aattattttt aaaagaaat ctggtcttgt tagaaaacaa aatttatttt tgtgctcatt | | 4395 |
| taagtttcaa acttactatt ttgacagtta ttttgataac aatgacacta gaaaacttga | | 4455 |
| ctccatttca tcattgtttc tgcatgaata tcatacaaat cagttagttt ttaggtcaag | | 4515 |
| ggcttactat ttctgggtct tttgctacta agttcacatt agaattagtg ccagaatttt | | 4575 |
| aggaacttca gagatcgtgt attgagattt cttaaataat gcttcagata ttattgcttt | | 4635 |
| attgcttttt tgtattggtt aaaactgtac atttaaaatt gctatgttac tattttctac | | 4695 | aattaatagt tgtctattt taaaataaat tagttgttaa gagtc    4740

<210> SEQ ID NO 4
<211> LENGTH: 928
<212> TYPE: PRT
<213> ORGANISM: Homo sapiens
<220> FEATURE:
<223> OTHER INFORMATION: retinoblastoma 1 protein (RB1), retinoblastoma susceptibility protein, OSRC. p105-Rb, pRb, RB

<400> SEQUENCE: 4

```
Met Pro Pro Lys Thr Pro Arg Lys Thr Ala Ala Thr Ala Ala Ala Ala
 1               5                  10                  15

Ala Ala Glu Pro Pro Ala Pro Pro Pro Pro Pro Pro Pro Glu Glu Asp
             20                  25                  30

Pro Glu Gln Asp Ser Gly Pro Glu Asp Leu Pro Leu Val Arg Leu Glu
         35                  40                  45

Phe Glu Glu Thr Glu Glu Pro Asp Phe Thr Ala Leu Cys Gln Lys Leu
     50                  55                  60

Lys Ile Pro Asp His Val Arg Glu Arg Ala Trp Leu Thr Trp Glu Lys
 65                  70                  75                  80

Val Ser Ser Val Asp Gly Val Leu Gly Gly Tyr Ile Gln Lys Lys Lys
                 85                  90                  95

Glu Leu Trp Gly Ile Cys Ile Phe Ile Ala Arg Val Asp Leu Asp Glu
            100                 105                 110

Met Ser Phe Thr Leu Leu Ser Tyr Arg Lys Thr Tyr Glu Ile Ser Val
        115                 120                 125

His Lys Phe Phe Asn Leu Leu Lys Glu Ile Asp Thr Ser Thr Lys Val
    130                 135                 140

Asp Asn Ala Met Ser Arg Leu Leu Lys Lys Tyr Asp Val Leu Phe Ala
145                 150                 155                 160

Leu Phe Ser Lys Leu Glu Arg Thr Cys Glu Leu Ile Tyr Leu Thr Gln
                165                 170                 175

Pro Ser Ser Ser Ile Ser Thr Glu Ile Asn Ser Ala Leu Val Leu Lys
            180                 185                 190

Val Ser Trp Ile Thr Phe Leu Leu Ala Lys Gly Glu Val Leu Gln Met
        195                 200                 205

Glu Asp Asp Leu Val Ile Ser Phe Gln Leu Met Leu Cys Val Leu Asp
    210                 215                 220

Tyr Phe Ile Lys Leu Ser Pro Pro Met Leu Leu Lys Glu Pro Tyr Lys
225                 230                 235                 240

Thr Ala Val Ile Pro Ile Asn Gly Ser Pro Arg Thr Pro Arg Arg Gly
                245                 250                 255

Gln Asn Arg Ser Ala Arg Ile Ala Lys Gln Leu Glu Asn Asp Thr Arg
            260                 265                 270

Ile Ile Glu Val Leu Cys Lys Glu His Glu Cys Asn Ile Asp Glu Val
        275                 280                 285

Lys Asn Val Tyr Phe Lys Asn Phe Ile Pro Phe Met Asn Ser Leu Gly
    290                 295                 300

Leu Val Thr Ser Asn Gly Leu Pro Glu Val Glu Asn Leu Ser Lys Arg
305                 310                 315                 320

Tyr Glu Glu Ile Tyr Leu Lys Asn Lys Asp Leu Asp Arg Arg Leu Phe
                325                 330                 335

Leu Asp His Asp Lys Thr Leu Gln Thr Asp Ser Ile Asp Ser Phe Glu
            340                 345                 350
```

-continued

```
Thr Gln Arg Thr Pro Arg Lys Ser Asn Leu Asp Glu Glu Val Asn Ile
            355                 360                 365
Ile Pro Pro His Thr Pro Val Arg Thr Val Met Asn Thr Ile Gln Gln
370                 375                 380
Leu Met Met Ile Leu Asn Ser Ala Ser Asp Gln Pro Ser Glu Asn Leu
385                 390                 395                 400
Ile Ser Tyr Phe Asn Asn Cys Thr Val Asn Pro Lys Glu Ser Ile Leu
            405                 410                 415
Lys Arg Val Lys Asp Ile Gly Tyr Ile Phe Lys Glu Lys Phe Ala Lys
            420                 425                 430
Ala Val Gly Gln Gly Cys Val Glu Ile Gly Ser Gln Arg Tyr Lys Leu
            435                 440                 445
Gly Val Arg Leu Tyr Tyr Arg Val Met Glu Ser Met Leu Lys Ser Glu
450                 455                 460
Glu Glu Arg Leu Ser Ile Gln Asn Phe Ser Lys Leu Leu Asn Asp Asn
465                 470                 475                 480
Ile Phe His Met Ser Leu Leu Ala Cys Ala Leu Glu Val Val Met Ala
            485                 490                 495
Thr Tyr Ser Arg Ser Thr Ser Gln Asn Leu Asp Ser Gly Thr Asp Leu
            500                 505                 510
Ser Phe Pro Trp Ile Leu Asn Val Leu Asn Leu Lys Ala Phe Asp Phe
            515                 520                 525
Tyr Lys Val Ile Glu Ser Phe Ile Lys Ala Glu Gly Asn Leu Thr Arg
530                 535                 540
Glu Met Ile Lys His Leu Glu Arg Cys Glu His Arg Ile Met Glu Ser
545                 550                 555                 560
Leu Ala Trp Leu Ser Asp Ser Pro Leu Phe Asp Leu Ile Lys Gln Ser
            565                 570                 575
Lys Asp Arg Glu Gly Pro Thr Asp His Leu Glu Ser Ala Cys Pro Leu
            580                 585                 590
Asn Leu Pro Leu Gln Asn Asn His Thr Ala Ala Asp Met Tyr Leu Ser
            595                 600                 605
Pro Val Arg Ser Pro Lys Lys Lys Gly Ser Thr Thr Arg Val Asn Ser
610                 615                 620
Thr Ala Asn Ala Glu Thr Gln Ala Thr Ser Ala Phe Gln Thr Gln Lys
625                 630                 635                 640
Pro Leu Lys Ser Thr Ser Leu Ser Leu Phe Tyr Lys Lys Val Tyr Arg
            645                 650                 655
Leu Ala Tyr Leu Arg Leu Asn Thr Leu Cys Glu Arg Leu Leu Ser Glu
            660                 665                 670
His Pro Glu Leu Glu His Ile Ile Trp Thr Leu Phe Gln His Thr Leu
            675                 680                 685
Gln Asn Glu Tyr Glu Leu Met Arg Asp Arg His Leu Asp Gln Ile Met
            690                 695                 700
Met Cys Ser Met Tyr Gly Ile Cys Lys Val Lys Asn Ile Asp Leu Lys
705                 710                 715                 720
Phe Lys Ile Ile Val Thr Ala Tyr Lys Asp Leu Pro His Ala Val Gln
            725                 730                 735
Glu Thr Phe Lys Arg Val Leu Ile Lys Glu Glu Glu Tyr Asp Ser Ile
            740                 745                 750
Ile Val Phe Tyr Asn Ser Val Phe Met Gln Arg Leu Lys Thr Asn Ile
            755                 760                 765
Leu Gln Tyr Ala Ser Thr Arg Pro Pro Thr Leu Ser Pro Ile Pro His
770                 775                 780
```

```
Ile Pro Arg Ser Pro Tyr Lys Phe Pro Ser Pro Leu Arg Ile Pro
785                 790                 795                 800

Gly Gly Asn Ile Tyr Ile Ser Pro Leu Lys Ser Pro Tyr Lys Ile Ser
            805                 810                 815

Glu Gly Leu Pro Thr Pro Thr Lys Met Thr Pro Arg Ser Arg Ile Leu
            820                 825                 830

Val Ser Ile Gly Glu Ser Phe Gly Thr Ser Glu Lys Phe Gln Lys Ile
        835                 840                 845

Asn Gln Met Val Cys Asn Ser Asp Arg Val Leu Lys Arg Ser Ala Glu
            850                 855                 860

Gly Ser Asn Pro Pro Lys Pro Leu Lys Lys Leu Arg Phe Asp Ile Glu
865                 870                 875                 880

Gly Ser Asp Glu Ala Asp Gly Ser Lys His Leu Pro Gly Glu Ser Lys
            885                 890                 895

Phe Gln Gln Lys Leu Ala Glu Met Thr Ser Thr Arg Thr Arg Met Gln
            900                 905                 910

Lys Gln Lys Met Asn Asp Ser Met Asp Thr Ser Asn Lys Glu Glu Lys
            915                 920                 925

<210> SEQ ID NO 5
<211> LENGTH: 39
<212> TYPE: DNA
<213> ORGANISM: Artificial Sequence
<220> FEATURE:
<223> OTHER INFORMATION: synthetic PCR primer used for wild-type
      plasmids

<400> SEQUENCE: 5
aagcttgcgg ccgcgatgga gccgctgaag gtggaaaag                              39

<210> SEQ ID NO 6
<211> LENGTH: 36
<212> TYPE: DNA
<213> ORGANISM: Artificial Sequence
<220> FEATURE:
<223> OTHER INFORMATION: synthetic PCR primer used for wild-type
      plasmids

<400> SEQUENCE: 6
ggtacctcta gattaggatg ctctgatgtt ggcgtc                                 36

<210> SEQ ID NO 7
<211> LENGTH: 32
<212> TYPE: DNA
<213> ORGANISM: Artificial Sequence
<220> FEATURE:
<223> OTHER INFORMATION: synthetic PCR primer used for
      FLAG-SMYD3-deltaN44 mutant plasmid

<400> SEQUENCE: 7
ggggtacctt aggatgctct gatgttggcg tc                                     32

<210> SEQ ID NO 8
<211> LENGTH: 39
<212> TYPE: DNA
<213> ORGANISM: Artificial Sequence
<220> FEATURE:
<223> OTHER INFORMATION: synthetic PCR primer used for
      FLAG-SMYD3-deltaN44 mutant plasmid

<400> SEQUENCE: 8
cggaattctg gcgcgatgga gccgctgaag gtggaaaag                              39
```

-continued

<210> SEQ ID NO 9
<211> LENGTH: 32
<212> TYPE: DNA
<213> ORGANISM: Artificial Sequence
<220> FEATURE:
<223> OTHER INFORMATION: synthetic PCR primer used for
      FLAG-SMYD3-deltaN99 mutant plasmid

<400> SEQUENCE: 9
cggaattctg actccgttcg acttcttggc ag                                 32

<210> SEQ ID NO 10
<211> LENGTH: 36
<212> TYPE: DNA
<213> ORGANISM: Artificial Sequence
<220> FEATURE:
<223> OTHER INFORMATION: synthetic PCR primer used for
      FLAG-SMYD3-deltaN244 mutant plasmid

<400> SEQUENCE: 10
cggaattctc ggaagcagct gagggaccag tactgc                             36

<210> SEQ ID NO 11
<211> LENGTH: 34
<212> TYPE: DNA
<213> ORGANISM: Artificial Sequence
<220> FEATURE:
<223> OTHER INFORMATION: synthetic PCR primer used for
      FLAG-SMYD3-deltaN34 mutant plasmid

<400> SEQUENCE: 11
cggaattcac ccttggcgta cacggtgtgc aagg                               34

<210> SEQ ID NO 12
<211> LENGTH: 7
<212> TYPE: PRT
<213> ORGANISM: Artificial Sequence
<220> FEATURE:
<223> OTHER INFORMATION: synthetic conserved Suppressor of variegation
      3-9 (Su 3-9), Enhancer-of-zeste, Trithorax (SET) domain
<221> NAME/KEY: VARIANT
<222> LOCATION: (5)...(6)
<223> OTHER INFORMATION: Xaa = any amino acid

<400> SEQUENCE: 12

Asn His Ser Cys Xaa Xaa Asn
 1               5

<210> SEQ ID NO 13
<211> LENGTH: 8
<212> TYPE: PRT
<213> ORGANISM: Artificial Sequence
<220> FEATURE:
<223> OTHER INFORMATION: synthetic conserved Suppressor of variegation
      3-9 (Su 3-9), Enhancer-of-zeste, Trithorax (SET) domain
<221> NAME/KEY: VARIANT
<222> LOCATION: (5)...(7)
<223> OTHER INFORMATION: Xaa = any amino acid

<400> SEQUENCE: 13

Gly Glu Glu Leu Xaa Xaa Xaa Tyr
 1               5

<210> SEQ ID NO 14
<211> LENGTH: 6
<212> TYPE: PRT
<213> ORGANISM: Artificial Sequence
<220> FEATURE:
<223> OTHER INFORMATION: synthetic 6xHis peptide

```
<400> SEQUENCE: 14

His His His His His His
 1               5

<210> SEQ ID NO 15
<211> LENGTH: 23
<212> TYPE: PRT
<213> ORGANISM: Artificial Sequence
<220> FEATURE:
<223> OTHER INFORMATION: synthetic Suppressor of variegation 3-9
      (Su 3-9), Enhancer-of-zeste, Trithorax (SET) SET-N domain
      from histone methyltransferase SMYD3

<400> SEQUENCE: 15

Lys Val Glu Lys Phe Ala Thr Ala Asn Arg Gly Asn Gly Leu Arg Ala
 1               5                  10                  15

Val Thr Pro Leu Arg Pro Gly
                20

<210> SEQ ID NO 16
<211> LENGTH: 23
<212> TYPE: PRT
<213> ORGANISM: Artificial Sequence
<220> FEATURE:
<223> OTHER INFORMATION: synthetic Suppressor of variegation 3-9
      (Su 3-9), Enhancer-of-zeste, Trithorax (SET) SET-N domain
      from histone methyltransferase DIM-5_Nc

<400> SEQUENCE: 16

Pro Leu Gln Ile Phe Arg Thr Lys Asp Arg Gly Trp Gly Val Lys Cys
 1               5                  10                  15

Pro Val Asn Ile Lys Arg Gly
                20

<210> SEQ ID NO 17
<211> LENGTH: 25
<212> TYPE: PRT
<213> ORGANISM: Artificial Sequence
<220> FEATURE:
<223> OTHER INFORMATION: synthetic Suppressor of variegation 3-9
      (Su 3-9), Enhancer-of-zeste, Trithorax (SET) SET-N domain
      from histone methyltransferase SET7/9_Hs

<400> SEQUENCE: 17

Arg Val Tyr Val Ala Glu Ser Leu Ile Ser Ser Ala Gly Glu Gly Leu
 1               5                  10                  15

Phe Ser Lys Val Ala Val Gly Pro Asn
                20                  25

<210> SEQ ID NO 18
<211> LENGTH: 23
<212> TYPE: PRT
<213> ORGANISM: Artificial Sequence
<220> FEATURE:
<223> OTHER INFORMATION: synthetic Suppressor of variegation 3-9
      (Su 3-9), Enhancer-of-zeste, Trithorax (SET) SET-N domain
      from histone methyltransferase Cir4_Sp

<400> SEQUENCE: 18

Pro Leu Glu Ile Phe Lys Thr Lys Glu Lys Gly Trp Gly Val Arg Ser
 1               5                  10                  15

Leu Arg Phe Ala Pro Ala Gly
                20

<210> SEQ ID NO 19
```

-continued

```
<211> LENGTH: 23
<212> TYPE: PRT
<213> ORGANISM: Artificial Sequence
<220> FEATURE:
<223> OTHER INFORMATION: synthetic Suppressor of variegation 3-9
      (Su 3-9), Enhancer-of-zeste, Trithorax (SET) SET-N domain
      from histone methyltransferase SET1_Sc

<400> SEQUENCE: 19

Pro Val Met Phe Ala Arg Ser Ala Ile His Asn Trp Gly Leu Tyr Ala
  1               5                  10                  15

Leu Asp Ser Ile Ala Ala Lys
             20

<210> SEQ ID NO 20
<211> LENGTH: 23
<212> TYPE: PRT
<213> ORGANISM: Artificial Sequence
<220> FEATURE:
<223> OTHER INFORMATION: synthetic Suppressor of variegation 3-9
      (Su 3-9), Enhancer-of-zeste, Trithorax (SET) SET-N domain
      from histone methyltransferase SET2_Sc

<400> SEQUENCE: 20

Pro Ile Ala Ile Phe Lys Thr Lys His Lys Gly Tyr Gly Val Arg Ala
  1               5                  10                  15

Glu Gln Asp Ile Glu Ala Asn
             20

<210> SEQ ID NO 21
<211> LENGTH: 23
<212> TYPE: PRT
<213> ORGANISM: Artificial Sequence
<220> FEATURE:
<223> OTHER INFORMATION: synthetic Suppressor of variegation 3-9
      (Su 3-9), Enhancer-of-zeste, Trithorax (SET) SET-N domain
      from histone methyltransferase G9a_Hs

<400> SEQUENCE: 21

Arg Leu Gln Leu Tyr Arg Thr Ala Lys Met Gly Trp Gly Val Arg Ala
  1               5                  10                  15

Leu Gln Thr Ile Pro Gln Gly
             20

<210> SEQ ID NO 22
<211> LENGTH: 24
<212> TYPE: PRT
<213> ORGANISM: Artificial Sequence
<220> FEATURE:
<223> OTHER INFORMATION: synthetic Suppressor of variegation 3-9
      (Su 3-9), Enhancer-of-zeste, Trithorax (SET) SET-N domain
      from histone methyltransferase SUV39H1_Hs

<400> SEQUENCE: 22

Asp Leu Cys Ile Phe Arg Thr Asp Asp Gly Arg Gly Trp Gly Val Arg
  1               5                  10                  15

Thr Leu Glu Lys Ile Arg Lys Asn
             20

<210> SEQ ID NO 23
<211> LENGTH: 23
<212> TYPE: PRT
<213> ORGANISM: Artificial Sequence
<220> FEATURE:
<223> OTHER INFORMATION: synthetic Suppressor of variegation 3-9
      (Su 3-9), Enhancer-of-zeste, Trithorax (SET) SET-N domain
      from histone methyltransferase PR-SET7_At
```

-continued

```
<400> SEQUENCE: 23

Gly Met Lys Ile Asp Leu Ile Asp Gly Lys Gly Arg Gly Val Ile Ala
1               5                   10                  15

Thr Lys Gln Phe Ser Arg Gly
            20

<210> SEQ ID NO 24
<211> LENGTH: 24
<212> TYPE: PRT
<213> ORGANISM: Artificial Sequence
<220> FEATURE:
<223> OTHER INFORMATION: synthetic Suppressor of variegation 3-9
      (Su 3-9), Enhancer-of-zeste, Trithorax (SET) SET-N domain
      from histone methyltransferase EZH2_Hs

<400> SEQUENCE: 24

Lys His Leu Leu Leu Ala Pro Ser Asp Val Ala Gly Trp Gly Ile Phe
1               5                   10                  15

Ile Lys Asp Pro Val Gln Lys Asn
            20

<210> SEQ ID NO 25
<211> LENGTH: 23
<212> TYPE: PRT
<213> ORGANISM: Artificial Sequence
<220> FEATURE:
<223> OTHER INFORMATION: synthetic Suppressor of variegation 3-9
      (Su 3-9), Enhancer-of-zeste, Trithorax (SET) SET-N domain
      from histone methyltransferase KRP_At

<400> SEQUENCE: 25

Asn Leu Glu Val Phe Arg Ser Ala Lys Lys Gly Trp Ala Val Arg Ser
1               5                   10                  15

Trp Glu Tyr Ile Pro Ala Gly
            20

<210> SEQ ID NO 26
<211> LENGTH: 23
<212> TYPE: PRT
<213> ORGANISM: Artificial Sequence
<220> FEATURE:
<223> OTHER INFORMATION: synthetic Suppressor of variegation 3-9
      (Su 3-9), Enhancer-of-zeste, Trithorax (SET) SET-N domain
      from histone methyltransferase ASH1_Dm

<400> SEQUENCE: 26

Gly Val Glu Arg Phe Met Thr Ala Asp Lys Trp Gly Val Arg Thr
1               5                   10                  15

Lys Leu Pro Ile Ala Lys Gly
            20

<210> SEQ ID NO 27
<211> LENGTH: 23
<212> TYPE: PRT
<213> ORGANISM: Artificial Sequence
<220> FEATURE:
<223> OTHER INFORMATION: synthetic Suppressor of variegation 3-9
      (Su 3-9), Enhancer-of-zeste, Trithorax (SET) SET-N domain
      from histone methyltransferase SETDB1_Hs

<400> SEQUENCE: 27

Arg Leu Gln Leu Phe Lys Thr Gln Asn Lys Gly Trp Gly Ile Arg Cys
1               5                   10                  15

Leu Asp Asp Ile Ala Lys Gly
            20
```

```
<210> SEQ ID NO 28
<211> LENGTH: 23
<212> TYPE: PRT
<213> ORGANISM: Artificial Sequence
<220> FEATURE:
<223> OTHER INFORMATION: synthetic Suppressor of variegation 3-9
      (Su 3-9), Enhancer-of-zeste, Trithorax (SET) SET-N domain
      from histone methyltransferase MLL2_Hs

<400> SEQUENCE: 28

Ala Val Gly Val Tyr Arg Ser Ala Ile His Gly Arg Gly Leu Phe Cys
1               5                   10                  15

Lys Arg Asn Ile Asp Ala Gly
            20

<210> SEQ ID NO 29
<211> LENGTH: 10
<212> TYPE: PRT
<213> ORGANISM: Artificial Sequence
<220> FEATURE:
<223> OTHER INFORMATION: synthetic wild type (Wt) retinoblatoma 1 (RB1)
      conserved C-terminal substrate domain peptide

<400> SEQUENCE: 29

Pro Thr Pro Thr Lys Met Thr Pro Arg Ser
1               5                   10

<210> SEQ ID NO 30
<211> LENGTH: 16
<212> TYPE: PRT
<213> ORGANISM: Artificial Sequence
<220> FEATURE:
<223> OTHER INFORMATION: synthetic wild type (Wt) retinoblatoma 1 (RB1)
      conserved C-terminal substrate domain peptide

<400> SEQUENCE: 30

Glu Ala Asp Gly Ser Lys His Leu Pro Gly Glu Ser Lys Phe Gln Gln
1               5                   10                  15

<210> SEQ ID NO 31
<211> LENGTH: 10
<212> TYPE: PRT
<213> ORGANISM: Artificial Sequence
<220> FEATURE:
<223> OTHER INFORMATION: synthetic K824A retinoblatoma 1 (RB1)
      C-terminal substrate domain peptide

<400> SEQUENCE: 31

Pro Thr Pro Thr Ala Met Thr Pro Arg Ser
1               5                   10

<210> SEQ ID NO 32
<211> LENGTH: 16
<212> TYPE: PRT
<213> ORGANISM: Artificial Sequence
<220> FEATURE:
<223> OTHER INFORMATION: synthetic K889A mutated retinoblatoma 1 (RB1)
      C-terminal substrate domain peptide

<400> SEQUENCE: 32

Glu Ala Asp Gly Ser Ala His Leu Pro Gly Glu Ser Lys Phe Gln Gln
1               5                   10                  15

<210> SEQ ID NO 33
<211> LENGTH: 16
<212> TYPE: PRT
<213> ORGANISM: Artificial Sequence
<220> FEATURE:
```

-continued

```
<223> OTHER INFORMATION: synthetic K896A mutated retinoblatoma 1 (RB1)
      C-terminal substrate domain peptide

<400> SEQUENCE: 33

Glu Ala Asp Gly Ser Lys His Leu Pro Gly Glu Ser Ala Phe Gln Gln
1               5                   10                  15

<210> SEQ ID NO 34
<211> LENGTH: 34
<212> TYPE: PRT
<213> ORGANISM: Artificial Sequence
<220> FEATURE:
<223> OTHER INFORMATION: synthetic SMYD3-wt wild type conserved
      Suppressor of variegation 3-9 (Su 3-9), Enhancer-of-zeste,
      Trithorax (SET) SET-N region

<400> SEQUENCE: 34

Met Glu Pro Leu Lys Val Glu Lys Phe Ala Thr Ala Asn Arg Gly Asn
1               5                   10                  15

Gly Leu Arg Ala Val Thr Pro Leu Arg Pro Gly Glu Leu Leu Phe Arg
            20                  25                  30

Ser Asp

<210> SEQ ID NO 35
<211> LENGTH: 34
<212> TYPE: PRT
<213> ORGANISM: Artificial Sequence
<220> FEATURE:
<223> OTHER INFORMATION: synthetic SMYD3-SETNm1 mutated Suppressor of
      variegation 3-9 (Su 3-9), Enhancer-of-zeste,
      Trithorax (SET) SET-N region

<400> SEQUENCE: 35

Met Glu Pro Leu Lys Val Glu Lys Phe Ala Thr Ala Asn Arg Ala Asn
1               5                   10                  15

Ala Leu Arg Ala Val Thr Pro Leu Arg Pro Gly Glu Leu Leu Phe Arg
            20                  25                  30

Ser Asp

<210> SEQ ID NO 36
<211> LENGTH: 34
<212> TYPE: PRT
<213> ORGANISM: Artificial Sequence
<220> FEATURE:
<223> OTHER INFORMATION: synthetic SMYD3-SETNm2 mutated Suppressor of
      variegation 3-9 (Su 3-9), Enhancer-of-zeste,
      Trithorax (SET) SET-N region

<400> SEQUENCE: 36

Met Glu Pro Leu Lys Val Glu Lys Phe Ala Thr Ala Asn Arg Ala Asn
1               5                   10                  15

Gly Leu Arg Ala Val Thr Pro Leu Arg Pro Gly Glu Leu Leu Phe Arg
            20                  25                  30

Ser Asp

<210> SEQ ID NO 37
<211> LENGTH: 34
<212> TYPE: PRT
<213> ORGANISM: Artificial Sequence
<220> FEATURE:
<223> OTHER INFORMATION: synthetic SMYD3-SETNm3 mutated Suppressor of
      variegation 3-9 (Su 3-9), Enhancer-of-zeste,
      Trithorax (SET) SET-N region

<400> SEQUENCE: 37
```

```
Met Glu Pro Leu Lys Val Glu Lys Phe Ala Thr Ala Asn Arg Gly Asn
1               5                   10                  15

Gly Leu Arg Ala Val Thr Pro Leu Arg Pro Ala Glu Leu Leu Phe Arg
            20                  25                  30

Ser Asp

<210> SEQ ID NO 38
<211> LENGTH: 10
<212> TYPE: PRT
<213> ORGANISM: Artificial Sequence
<220> FEATURE:
<223> OTHER INFORMATION: synthetic 10xHis peptide

<400> SEQUENCE: 38

His His His His His His His His His His
1               5                   10
```

METHODS OF MODULATING SMYD3 FOR TREATMENT OF CANCER

CROSS-REFERENCES TO RELATED APPLICATIONS

This application is a U.S. National Stage Application of PCT/JP2006/313038, filed Jun. 23, 2006, which claims the benefit of U.S. Provisional Application Ser. No. 60/695,957 filed Jul. 1, 2005, all of which are hereby incorporated by reference in their entirety.

TECHNICAL FIELD

The present invention relates to transcriptional regulation, more particularly to the identification of agents that modulate methyltransferase activity, such as agents that modulate methylation of retinoblastoma by SMYD3 (also known as "ZNFN3A1"). As SMYD3 is up-regulated in a number of cancer types, SMYD3 modulators so identified may prove useful in the treatment of cancer, including, for example, colorectal carcinoma, hepatocellular carcinoma, breast cancer and bladder cancer.

BACKGROUND ART

Recent molecular studies have disclosed that abrogated cell cycle control underlies a wide range of human tumors (Sherr, C. J., *Science* 274, 1672-7 (1996)). Genetic alteration in p53, RB1, or p16 genes is involved in a great majority of human cancers, where deregulated cell cycle progression results in uncontrolled cell proliferation (Hanahan, D. & Weinberg, R. A. *Cell* 100, 57-70 (2000); Sherr, C. J. & McCormick, F. *Cancer Cell* 2, 103-12 (2002)). Among the cell cycling, the $G_1$/S boundary, wherein cell cycle is arrested, integrity of the genome is surveyed, and DNA damages are repaired, is critical for the maintenance of normal cellular and genomic properties. Two key signaling pathways, namely p53 and RB1, participate in the regulation of the $G_1$/S boundary by controlling a number of downstream genes. Cells containing damaged DNA are arrested at this boundary by the induction p21$^{Cip1}$ through transactivation of accumulated wild type p53 protein (Sherr, C. J. & Roberts, J. M. *Genes Dev* 13, 1501-12 (1999)). Isolated as a responsible gene for familial retinoblastoma (Friend, S. H. et al. *Nature* 323, 643-6 (1986).; Fung, Y. K. et al. *Science* 236, 1657-61 (1987); Lee, W. H. et al. *Science* 235, 1394-9 (1987)), RB1 functions as a tumor suppressor through the control of cell cycle progression. From the $G_1$ to the S cell cycle transition, RB1 is inactivated by phosphorylation, which is catalyzed by cyclin dependent kinases (CDKs). Under phosphorylated RB1 inhibits the activator E2Fs, transcription factors that modulate expression of genes required for DNA replication and cell cycle progression (Dannenberg, J. H., et al., *Genes Dev* 14, 3051-64 (2000).; Sage, J. et al. *Genes Dev* 14, 3037-50 (2000)), by a direct interaction with their activation domain, alteration of chromatin structure complexed with HDACs, and recruitment of a repressor complex to E2F-binding site(s) in the promoter region of responsive genes (Weintraub, S. J., et al., *Nature* 358, 259-61 (1992).; Sellers, W. R., et al., *Proc Natl Acad Sci USA* 92, 11544-8 (1995)). Phosphorylated by CDK/cyclin complexes, such as CDK4/cyclinD, RB1 dissociates E2Fs, which then transactivate downstream genes including cyclin E, c-Myb, CDK2, and BCL2.

The present inventors previously reported that SMYD3 has a di- and tri-methyltransferase activity on lysine 4 of histone H3 (H3-K4), and that elevated SMYD3 expression plays a crucial role in the proliferation of colorectal carcinoma (CRC) and hepatocellular carcinoma (HCC) cells (Hamamoto, R. et al., *Nat Cell Biol* 6, 731-40 (2004)), because over-expression of SMYD3 resulted in growth promotion of NIH3T3 cells and the knockdown of endogenous SMYD3 expression in several cancer cells induced a growth inhibition and apoptosis of those cells. However, the precise mechanism(s) by which SMYD3-overexpression results in growth promotion remains unresolved. Modification of histones by acetylation, phosphorylation, and/or methylation regulates chromatin structure that leads to transcriptional activation or inactivation of target gene(s) by recruiting different molecules. Regarding histone lysine methylation, modification of H3-K4, H3-K36, and H3-K79 is associated with a transcriptional activation by the conformational change from heterochromatin to euchromatin structure (Im, H. et al., *J Biol Chem* 278, 18346-52 (2003); Bannister, A. J. et al., *J Biol Chem* 280, 17732-6 (2005).; Schneider, R. et al., *Nat Cell Biol* 6, 73-7 (2004)), whereas methylation of H3-K9, H3-K27, and H4-K20 results in transcriptional repression by heterochromatin structure (Schotta, G. et al., *Genes Dev* 18, 1251-62 (2004).; Nakayama, J. et al., *Science* 292, 110-3 (2001).; Kirmizis, A. et al. *Genes Dev* 18, 1592-605 (2004)).

SUMMARY OF THE INVENTION

The present invention is based, at least in part, on the discovery of a novel mechanism of RB1 regulation through lysine 824 methylation by SMYD3. SMYD3, also known under the gene name "ZNFN3A1", is a histone H3 methyltransferase that is up-regulated in a great majority of colorectal and hepatocellular carcinomas (See, for example, WO 2003/027413) as well as bladder and breast cancers.

The C-terminal region of RB1 interacts with the SET domain of SMYD3. Furthermore, expression of SMYD3 enhanced the phosphorylation of 821/826 and 807/811 of RB1 by CDK2/cyclinE or CDK6/cyclinD3 complex in vitro and in vivo, which, in turn, resulted in augmented transcriptional activity of E2F in HEK293 cells. This data implies that enhanced SMYD3 expression promotes cell cycle progression through the modification of RB1 and subsequent transcriptional activation of E2F in cancer cells. The instant findings suggest a novel mechanism underlying the regulation of RB1. In addition, the present findings contribute to the better understanding of carcinogenesis, more particularly colorectal, hepatocellular, bladder and breast carcinogenesis, and thus contribute to the development new therapeutic strategies for these tumors.

Accordingly, it is an object of the present invention to provide a method for identifying an agent that modulates methylation of retinoblastoma by SMYD3, the method including the steps of:

(a) contacting an SMYD3 polypeptide having a methyltransferase activity with a retinoblastoma peptide to be methylated and a cofactor in the presence of a test agent under conditions suitable for the methylation of the retinoblastoma peptide;

(b) detecting the methylation level of the retinoblastoma peptide; and (c) comparing the methylation level detected in step (b) with a control level detected in the absence of the agent wherein an increase or decrease in the methylation level as compared to the control level indicates that the agent modulates methylation of retinoblastoma by SMYD3.

It is a further object of the present invention to provide a kit for detecting for the ability of a test compound to regulate methylation of retinoblastoma, such a kit including (a) an SMYD3 polypeptide having methyl transferase activity, (b) a retinoblastoma peptide capable of being methylated by the SMYD3 polypeptide, and (c) a cofactor for the methylation of the retinoblastoma peptide. In a further embodiment, the kit may optionally include S-adenosyl homocysteine hydrolase (SAHH).

The present invention further provides a method of screening for a compound for treating a cancer, such as colorectal cancer, hepatocellular carcinoma, bladder cancer, and breast cancer, such a method including the steps of: (a) identifying a test compound that modulates methylation according to the method described above, and (b) selecting the test compound that decreases the methylation level of the substrate to be methylated as compared to a control methylation level detected in the absence of the test compound.

The present invention further provides a composition for alleviating a symptom of a cancer, such as colorectal cancer, hepatocellular carcinoma, bladder cancer, and breast cancer, such composition composed of a pharmaceutically effective amount of a compound identified by the method described above and a pharmaceutically acceptable carrier.

It is a further object of the present invention to provide a method for alleviating a symptom of a cancer, such as colorectal cancer, hepatocellular carcinoma, bladder cancer, and breast cancer, including the step of contacting the cancer cell with a pharmaceutically effective amount of a compound identified by the method described above.

These and other objects, features and advantages of the invention will become more fully apparent when the following detailed description is read in conjunction with the accompanying figures and examples, as well as the claims appended hereto.

Unless otherwise defined, all technical and scientific terms used herein have the same meaning as commonly understood by one of ordinary skill in the art to which this invention belongs. In addition, the words "a", "an" and "the" as used herein mean "at least one" unless otherwise specifically indicated.

Although methods and materials similar or equivalent to those described herein can be used in the practice or testing of the present invention, suitable methods and materials are described herein below.

All publications, patent applications, patents, and other references mentioned herein are incorporated by reference in their entirety. In case of conflict, the present specification, including definitions, will control. In addition, the materials, methods, and examples are illustrative only and not intended to be limiting.

DETAILED DESCRIPTION OF THE INVENTION

Figure 1:
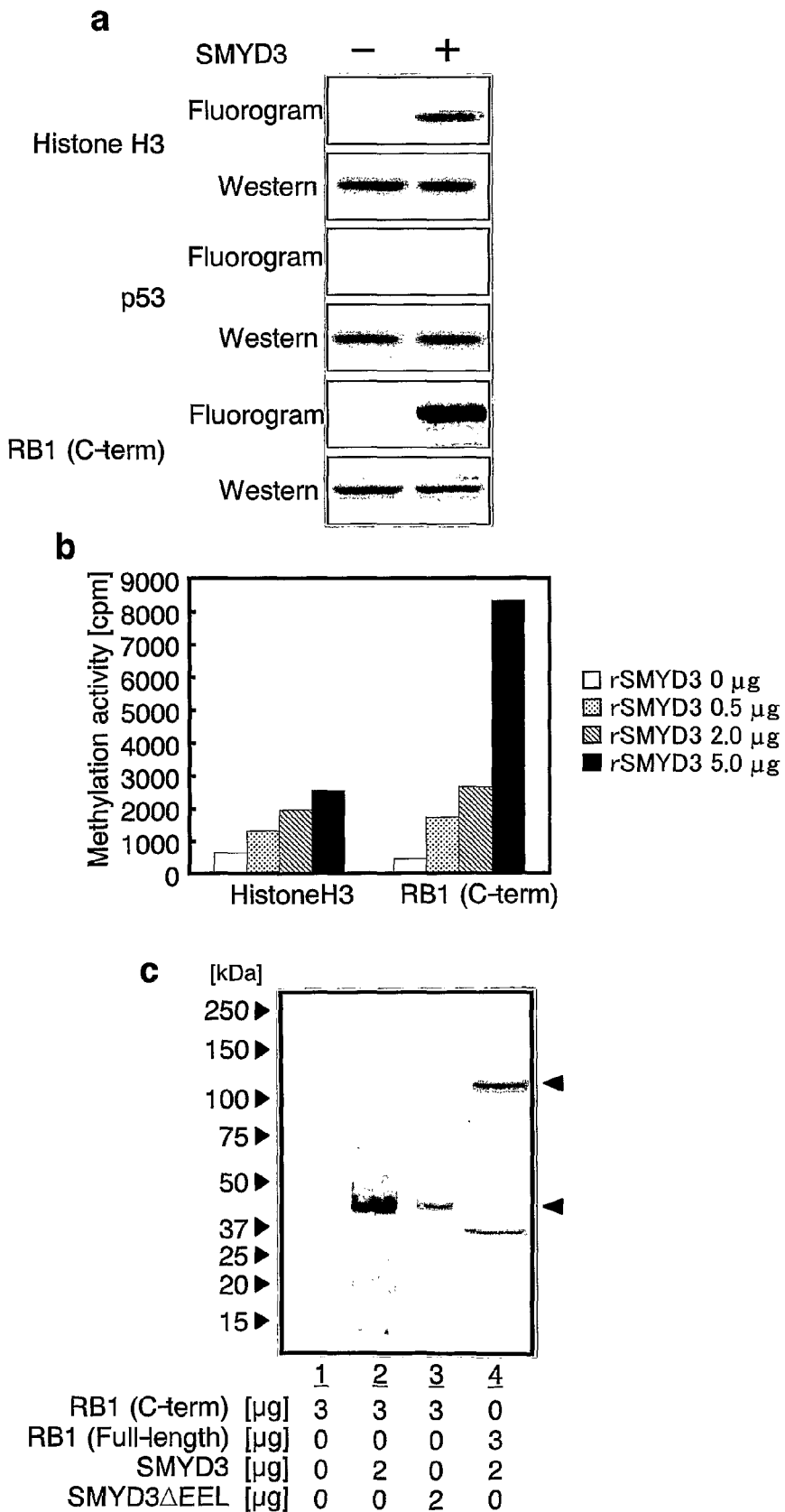
FIG. 1 depicts the MTase activity of SMYD3 on recombinant RB1 proteins. Part a depicts the results of an in vitro MTase assay using recombinant histone H3, p53, or C-terminal region of RB1 as substrate. Equal amount of substrate was incubated with immunoprecipitated Flag-tagged SMYD3 and $^3$H-labeled SAM, a methyl donor. Proteins were separated on SDS-PAGE, and methylated substrate was detected by fluorogram. Total amount of substrate was examined by immuno-blot analysis using specific antibody. Part b depicts the dose-dependent MTase activity of recombinant SMYD3 on histone H3 and C-terminal RB1 proteins. Part c depicts the MTase activity of SMYD3 on C-terminal and full-length RB1 (lane 2 and 4, respectively). Mutant SMYD3 containing a deletion in the conserved amino acids (SMYD3ΔEEL) markedly decreased the MTase activity (lane 3).

The SMYD3 cDNA consists of 1622 nucleotides that contain an open reading frame of 1284 nucleotides as set forth in SEQ ID NO:1. The open reading frame encodes a 428-amino acid protein with a zinc finger motif and a SET domain, as shown in SEQ ID NO:2. The zinc finger domain (MYND) extends from amino acid 49 to amino acid 87 and the SET (Su 3-9, Enhancer-of-zeste, Trithorrax) domain extends from amino acid 117 to amino acid 246.

The subcellular localization of the SMYD3 protein is altered during cell cycle progression and by the density of cultured cells. The SMYD3 protein accumulates in the nucleus when cells are in middle to late S phase or cultured in sparse conditions. However, the SMYD3 protein localizes in the cytoplasm as well as in the nucleus when cells are in other phases of the cell cycle or grown in a dense condition.

The present invention thus provides a method of screening for an agent that modulates SMYD3 methyltransferase activity. The method is practiced by contacting an SMYD3 polypeptide or a functional equivalent thereof having methyltransferase activity with a retinoblastoma protein, and assaying methyltransferase activity of the contacted SMYD3 or its functional equivalent. An agent that modulates methyltransferase activity of the SMYD3 or functional equivalent is thereby identified.

In the present invention, the term "functionally equivalent" means that the subject protein or polypeptide has the same or substantially the same methyltransferase activity as SMYD3. In particular, the protein catalyzes the methylation of a retinoblastoma protein or a fragment of a retinoblastoma protein that includes lysine 824. Whether a subject protein has the target activity can be routinely determined by the present invention. Namely, the methyltransferase activity can be determined by (a) contacting a polypeptide with a substrate (e.g., a retinoblastoma protein or a fragment that includes lysine 824) and a co-factor (e.g., S-adenosyl-L-methionine) under conditions suitable for methylation of the substrate, and (b) detecting the methylation level of the substrate.

As used herein, the term "retinoblastoma peptide" refers to fall length retinoblastoma proteins (e.g., SEQ ID NO: 4) as well as mutants and fragments thereof. Examples of functional fragments include, but are not limited to, C-terminal fragment such as the fragment composed of amino acids 769 to 921 of SEQ ID NO: 4. Preferred fragments include the lysine residue at position 824. Examples of functional mutants include, but are not limited to, the following RB1 mutants that retain the methylation capacity of the full length retinoblastoma protein: K889A, K896A, K791A, K814A, K791A/K824A, and K814A/K824A.

Methods for preparing proteins that are functional equivalents of a given protein are well known to those skilled in the art and include conventional methods of introducing mutations into the protein. For example, one skilled in the art can prepare proteins functionally equivalent to the human SMYD3 protein by introducing an appropriate mutation in the amino acid sequence of the human SMYD3 protein using site-directed mutagenesis for example (Hashimoto-Gotoh, T. et al. (1995), Gene 152, 271-275; Zoller, M J, and Smith, M. (1983), Methods Enzymol. 100, 468-500; Kramer, W. et al. (1984), Nucleic Acids Res. 12, 9441-9456; Kramer W, and Fritz H J. (1987) Methods. Enzymol. 154, 350-367; Kunkel, T A (1985), Proc. Natl. Acad. Sci. USA. 82, 488-492). Amino acid mutations can occur in nature, too. A SMYD3 polypeptide useful in the context of the present invention includes those proteins having the amino acid sequences of the human SMYD3 protein in which one or more amino acids are mutated, provided the resulting mutated proteins are functional equivalents of the human SMYD3 protein, more particularly retain the methyltransferase activity of the human SMYD3 protein. The number of amino acids to be mutated in such a mutant is generally 20 amino acids or less, typically 10 amino acids or less, preferably 6 amino acids or less, and more preferably 3 amino acids or less. To maintain the methyltransferase activity, the SET-domain "NHSCXXN" (SEQ ID NO:12) and "GEELXXXY" (SEQ ID NO:13) are preferably conserved in the amino acid sequence of the mutated proteins ("X" indicates any amino acid).

Mutated or modified proteins, i.e., proteins having amino acid sequences modified by deleting, adding and/or replacing one or more amino acid residues of a certain amino acid sequence, are known to retain the biological activity of the original protein (Mark, D. F. et al., Proc. Natl. Acad. Sci. USA (1984) 81, 5662-5666, Zoller, M. J. & Smith, M., Nucleic Acids Research (1982) 10, 6487-6500, Wang, A. et al., Science 224, 1431-1433, Dalbadie-McFarland, G. et al., Proc. Natl. Acad. Sci. USA (1982) 79, 6409-6413).

The amino acid residue to be mutated is preferably mutated into a different amino acid that allows the properties of the amino acid side-chain to be conserved (a process known as conservative amino acid substitution). Examples of properties of amino acid side chains include hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). Note, the parenthetic letters indicate the one-letter codes of amino acids.

An example of a protein in one or more amino acids residues are added to the amino acid sequence of human SMYD3 protein (SEQ ID NO: 2) is a fusion protein containing the human SMYD3 protein. Fusion proteins include fusions of the human SMYD3 protein and other peptides or proteins, and are used in the present invention. Fusion proteins can be made by techniques well known to a person skilled in the art, such as by linking the DNA encoding the human SMYD3 protein of the invention with DNA encoding other peptides or proteins, so that the frames match, inserting the fusion DNA into an expression vector and expressing it in a host. There is no restriction as to the peptides or proteins fused to the protein of the present invention.

Known peptides that can be used as peptides to be fused to the SMYD3 protein include, for example, FLAG (Hopp, T. P. et al., Biotechnology (1988) 6, 1204-1210), 6×His (SEQ ID NO:14) containing six His (histidine) residues, 10×His (SEQ ID NO:38), Influenza agglutinin (HA), human c-myc fragment, VSP-GP fragment, p18HIV fragment, T7-tag, HSV-tag, E-tag, SV40T antigen fragment, lck tag, α-tubulin fragment, B-tag, Protein C fragment, and the like. Examples of proteins that may be fused to a protein of the invention include GST (glutathione-S-transferase), Influenza agglutinin (HA), immunoglobulin constant region, β-galactosidase, MBP (maltose-binding protein), and such.

Fusion proteins can be prepared by fusing commercially available DNA, encoding the fusion peptides or proteins discussed above, with the DNA encoding the protein of the present invention and expressing the fused DNA prepared.

An alternative method known in the art to isolate functionally equivalent proteins uses hybridization techniques to identify homologous sequences (Sambrook, J. et al., Molecular Cloning 2nd ed. 9.47-9.58, Cold Spring Harbor Lab. Press, 1989). One skilled in the art can readily isolate a DNA having high homology with a whole or part of the SMYD3 DNA sequence (e.g., SEQ ID NO: 1) encoding the human SMYD3 protein, and isolate proteins that are functionally equivalent to the human SMYD3 protein from the isolated DNA. The proteins used for the present invention include those that are encoded by DNA that hybridize with a whole or part of the DNA sequence encoding the human SMYD3 protein and are functional equivalents of the human SMYD3 protein. These proteins include mammal homologues corresponding to the protein derived from human or mouse (for example, a protein encoded by a monkey, rat, rabbit and bovine gene). In isolating a cDNA highly homologous to the DNA encoding the human SMYD3 protein from animals, it is particularly preferable to use tissues from skeletal muscle, testis, HCC, or colorectal tumors.

The condition of hybridization for isolating a DNA encoding a functional equivalent of the human SMYD3 protein can be routinely selected by a person skilled in the art. For example, hybridization may be performed by conducting pre-hybridization at 68° C. for 30 min or longer using "Rapid-hyb buffer" (Amersham LIFE SCIENCE), adding a labeled probe, and warming at 68° C. for 1 hour or longer. The following washing step can be conducted, for example, in a low stringent condition. A low stringency condition is, for example, 42° C., 2×SSC, 0.1% SDS, or preferably 50° C., 2×SSC, 0.1% SDS. More preferably, highly stringent conditions are used. In the context of the present invention, a highly stringent condition includes, for example, washing 3 times in 2×SSC, 0.01% SDS at room temperature for 20 min, then washing 3 times in 1×SSC, 0.1% SDS at 37° C. for 20 min, and washing twice in 1×SSC, 0.1% SDS at 50° C. for 20 min. However, several factors such as temperature and salt concentration can influence the stringency of hybridization and one skilled in the art can suitably select the factors to achieve the requisite stringency.

In place of hybridization, a gene amplification method, for example, the polymerase chain reaction (PCR) method, can be utilized to isolate a DNA encoding a protein that is functionally equivalent to the human SMYD3 protein, using a primer synthesized based on the sequence information of the DNA (SEQ ID NO: 1) encoding the human SMYD3 protein (SEQ ID NO: 2).

Proteins that are functional equivalents of the human SMYD3 protein, encoded by DNA isolated through the above hybridization techniques or by gene amplification techniques, normally have a high homology to the amino acid sequence of the human SMYD3 protein. "High homology" (also referred to as "high identity") typically refers to the degree of identity between two optimally aligned sequences (either polypeptide or polynucleotide sequences). Typically, high homology or identity refers to homology of 40% or higher, preferably 60% or higher, more preferably 80% or higher, even more preferably 85%, 90%, 95%, 98%, 99%, or higher. The degree of homology or identity between two polypeptide or polynucleotide sequences can be determined by following the algorithm in "Wilbur, W. J. and Lipman, D. J. Proc. Natl. Acad. Sci. USA (1983) 80, 726-730".

A protein useful in the context of the present invention may have variations in amino acid sequence, molecular weight, isoelectric point, the presence or absence of sugar chains, or form, depending on the cell or host used to produce it or the purification method utilized. Nevertheless, so long as it is a function equivalent of human SMYD3 protein (SEQ ID NO: 2), it is useful in the present invention.

The proteins useful in the context of the present invention can be prepared as recombinant proteins or natural proteins, by methods well known to those skilled in the art. A recombinant protein can be prepared by inserting a DNA encoding a protein of the present invention (for example, the DNA comprising the nucleotide sequence of SEQ ID NO: 1), into an appropriate expression vector, introducing the vector into an appropriate host cell, obtaining the extract, and purifying the protein by subjecting the extract to chromatography, for example, ion exchange chromatography, reverse phase chromatography, gel filtration, or affinity chromatography utilizing a column to which antibodies against the protein of the present invention is fixed, or by combining more than one of aforementioned columns.

In addition, when a protein useful in the context of the present invention is expressed within host cells (for example, animal cells and *E. coli*) as a fusion protein with glutathione-S-transferase protein or as a recombinant protein supplemented with multiple histidines, the expressed recombinant protein can be purified using a glutathione column or nickel column.

After purifying the fusion protein, it is also possible to exclude regions other than the objective protein by cutting with thrombin or factor-Xa as required.

A natural protein can be isolated by methods known to a person skilled in the art, for example, by contacting an affinity column, in which antibodies binding to the SMYD3 protein described below are bound, with the extract of tissues or cells expressing the protein of the present invention. The antibodies can be polyclonal antibodies or monoclonal antibodies.

In the present invention, the methyltransferase activity of a SMYD3 polypeptide can be determined by methods known in the art. For example, a SMYD3 polypeptide and a retinoblastoma peptide substrate can be incubated with a labeled methyl donor, under suitable assay conditions. Examples of preferred methyl donors include, but are not limited to, S-adenosyl-[methyl-$^{14}$C]-L-methionine, and S-adenosyl-[methyl-$^{3}$H]-L-methionine preferably. Transfer of the radiolabel to the retinoblastoma peptide can be detected, for example, by SDS-PAGE electrophoresis and fluorography. Alternatively, following the reaction, the retinoblastoma peptides can be separated from the methyl donor by filtration, and the amount of radiolabel retained on the filter quantitated by scintillation counting. Other suitable labels that can be attached to methyl donors, such as chromogenic and fluorescent labels, and methods of detecting transfer of these labels to retinoblastoma peptides, are known in the art.

Alternatively, the methyltransferase activity of SMYD3 can be determined using an unlabeled methyl donor (e.g. S-adenosyl-L-methionine) and reagents that selectively recognize methylated retinoblastoma peptides. For example, after incubation of SMYD3, substrate to be methylated and methyl donor, under conditions suitable for methylation of the substrate, methylated substrate can be detected using conventional immunological methods. Any immunological techniques that uses an antibody to recognize a methylated substrate can be used for the detection.

Furthermore, it was confirmed that phosphorylation of RB1 at Ser 807 and Ser 811 was enhanced in the methlated RB1 at Lys 824. Accordingly, in another embodiments, methylation level of the RB1 may be estimated via phosphorylation of RB1. Kinase such as CDK2 or CDK6 may also be required for the phosphorylation of RB1. The phosphorylation of RB1 may be detected using radiolabeled phosphate donor. Alternatively, antibody recognising phosphorylation site of RB1 may be used for estimating phosphorylation level of RB1.

Various low-throughput and high-throughput enzyme assay formats are known in the art and can be readily adapted for detection or measuring of the methyltransferase activity of SMYD3. For high-throughput assays, the retinoblastoma peptide substrate can conveniently be immobilized on a solid support, such as a multiwell plate, slide or chip. Following the reaction, the methylated product can be detected on the solid support by the methods described above. Alternatively, the methyltransferase reaction can take place in solution, after which the retinoblastoma peptide can be immobilized on a solid support, and the methylated product detected. To facilitate such assays, the solid support can be coated with streptavidin and the retinoblastoma labeled with biotin, or the solid support can be coated with anti-retinoblastoma antibodies. The skilled person can determine suitable assay formats depending on the desired throughput capacity of the screen.

The present invention also encompasses the use of partial peptides of a protein of the present invention. A partial peptide has an amino acid sequence specific to the SMYD3 protein and consists of less than about 400 amino acids, usually less than about 200 and often less than about 100 amino acids, and at least about 7 amino acids, preferably about 8 amino acids or more, and more preferably about 9 amino acids or more. The partial peptide can be used, for example, in the screening for an agent or compound that binds to the SMYD3 protein, and the screening for inhibitors of the binding between SMYD3 and a co-factor thereof, such as, for example, SAM. The partial peptide containing the SET-domain is preferably used for such screening.

A partial peptide useful in the context of the present invention can be produced by genetic engineering, by known methods of peptide synthesis, or by digesting the protein of the invention with an appropriate peptidase. For peptide synthesis, for example, solid phase synthesis or liquid phase synthesis may be used.

A SMYD3 mutant having a mutation of SET-domain shows inhibitory effects on cell proliferation. Therefore, a partial peptide of SMYD3 preferably includes the SET-domain "NHSCXXN" (SEQ ID NO:12) and/or "GEELXXXY" (SEQ ID NO:13).

Any test agent can be used. Examples include, but are not limited to, cell extracts, cell culture supernatant, products of fermenting microorganism, extracts from marine organism, plant extracts, purified or crude proteins, peptides, non-peptide compounds, synthetic micromolecular compounds and natural compounds.

Test agents or compounds useful in the assays described herein can also take the form of antibodies that specifically bind to SMYD3 or partial SMYD3 peptides that lack methyltransferase activity. For example, antibodies (e.g., monoclonal antibodies) can be tested for the ability to block the binding between SMYD3 and its retinoblastoma substrate.

An agent or compound isolated by the screening methods of the present invention is a candidate for drugs that inhibit the methyltransferase activity of SMYD3 and, thus, can be applied to the treatment or prevention of hepatocellular, colorectal, breast and/or bladder cancer.

Moreover, agents or compounds in which a part of the structure of the agent or compound inhibiting the methyltransferase activity of SMYD3 is converted by addition, deletion and/or replacement are also included in the agents and compounds obtainable by the screening methods of the present invention.

As noted above, the agents or compounds that inhibit the methyltransferase activity of SMYD3 can be either partial peptides that lack the methyltransferase activity of SMYD3 or can be antibodies against SMYD3. As used herein, the term "antibody" refers to an immunoglobulin molecule having a specific structure, that interacts (i.e., binds) only with the antigen that was used for synthesizing the antibody or with an antigen closely related thereto. Furthermore, an antibody may be a fragment of an antibody or a modified antibody, so long as it binds to the proteins encoded by SMYD3 gene. For instance, the antibody fragment may be Fab, F(ab')$_2$, Fv, or single chain Fv (scFv), in which Fv fragments from H and L chains are ligated by an appropriate linker (Huston J. S. et al. *Proc. Natl. Acad. Sci. U.S.A.* 85:5879-5883 (1988)). More specifically, an antibody fragment may be generated by treating an antibody with an enzyme, such as papain or pepsin. Alternatively, a gene encoding the antibody fragment may be constructed, inserted into an expression vector, and expressed in an appropriate host cell (see, for example, Co M. S. et al. J. Immunol. 152:2968-2976 (1994); Better M. and Horwitz A. H. Methods Enzymol. 178:476-496 (1989); Pluckthun A. and Skerra A. Methods Enzymol. 178:497-515 (1989); Lamoyi E. Methods Enzymol. 121:652-663 (1986); Rousseaux J. et al. Methods Enzymol. 121:663-669 (1986); Bird R. E. and Walker B. W. Trends Biotechnol. 9:132-137 (1991)).

An antibody may be modified by conjugation with a variety of molecules, such as polyethylene glycol (PEG). The present invention provides such modified antibodies. The modified antibody can be obtained by chemically modifying an antibody. Such modification methods are conventional in the field. Alternatively, an antibody may comprise as a chimeric antibody having a variable region derived from a nonhuman antibody and a constant region derived from a human antibody, or a humanized antibody, comprising a complementarity determining region (CDR) derived from a nonhuman antibody, the frame work region (FR) derived from a human antibody and the constant region. Such antibodies can be prepared by using known technologies. Humanization can be performed by substituting rodent CDRs or CDR sequences for the corresponding sequences of a human antibody (see e.g., Verhoeyen et al., *Science* 239:1534-1536 (1988)). Accordingly, such humanized antibodies are chimeric antibodies, wherein substantially less than an intact human variable domain has been substituted by the corresponding sequence from a non-human species.

Fully human antibodies, comprising human variable regions in addition to human framework and constant regions, can also be used. Such antibodies can be produced using various techniques that are known in the art. For example, in vitro methods involving the use of recombinant libraries of human antibody fragments displayed on bacteriophage may be used (e.g., Hoogenboom & Winter, J. Mol. Biol. 227:381 (1991)). Similarly, human antibodies can be made by introducing of human immunoglobulin loci into transgenic animals, e.g., mice in which the endogenous immunoglobulin genes have been partially or completely inactivated. This approach is described, e.g., in U.S. Pat. Nos. 6,150,584; 5,545,807; 5,545,806; 5,569,825; 5,625,126; 5,633,425; 5,661,016.

When administrating an agent or compound isolated by a method of the present invention as a pharmaceutical for humans and other mammals, such as mice, rats, guinea-pigs, rabbits, cats, dogs, sheep, pigs, cattle, monkeys, baboons, and chimpanzees, the isolated agent or compound can be directly administered or can be formulated into a dosage form using known pharmaceutical preparation methods. For example, according to the need, the drugs can be taken orally, as sugar-coated tablets, capsules, elixirs and microcapsules, or non-orally, in the form of injections of sterile solutions or suspensions with water or any other pharmaceutically acceptable liquid. For example, the agents or compounds can be mixed with pharmaceutically acceptable carriers or media, specifically, sterilized water, physiological saline, plant-oils, emulsifiers, suspending agents, surfactants, stabilizers, flavoring agents, excipients, vehicles, preservatives, binders, and such, in a unit dose form required for generally accepted drug implementation. The amount of active ingredients in these preparations makes a suitable dosage within the indicated range acquirable.

Examples of additives that can be mixed to tablets and capsules are, binders such as gelatin, corn starch, tragacanth gum and arabic gum; excipients such as crystalline cellulose; swelling agents such as corn starch, gelatin and alginic acid; lubricants such as magnesium stearate; sweeteners such as sucrose, lactose or saccharin; and flavoring agents such as peppermint, Gaultheria adenothrix oil and cherry. When the unit-dose form is a capsule, a liquid carrier, such as an oil, can also be further included in the above ingredients. Sterile composites for injections can be formulated following normal drug implementations using vehicles such as distilled water used for injections.

Physiological saline, glucose, and other isotonic liquids including adjuvants, such as D-sorbitol, D-mannose, D-mannitol, and sodium chloride, can be used as aqueous. solutions for injections. These can be used in conjunction with suitable solubilizers, such as alcohol, specifically ethanol, polyalcohols such as propylene glycol and polyethylene glycol, nonionic surfactants, such as Polysorbate 80 (™) and HCO-50.

Sesame oil or soy-bean oil can be used as a oleaginous liquid and may be used in conjunction with benzyl benzoate or benzyl alcohol as a solubilizer and may be formulated with a buffer, such as phosphate buffer and sodium acetate buffer; a pain-killer, such as procaine hydrochloride; a stabilizer, such as benzyl alcohol and phenol; and an anti-oxidant. The prepared injection may be filled into a suitable ampule.

Methods well known to one skilled in the art may be used to administer a pharmaceutical composition of the present invention to patients, for example as intraarterial, intravenous, or percutaneous injections and also as intranasal, intramuscular or oral administrations. The dosage and method of administration vary according to the body-weight and age of a patient and the administration method; however, one skilled in the art can routinely select a suitable method of administration. In addition, if the agent or compound of interest is encodable by a DNA, the DNA can be inserted into a vector for gene therapy and the vector administered to a patient to perform the therapy. The dosage and method of administration vary according to the body-weight, age, and symptoms of the patient but one skilled in the art can suitably select them.

For example, although the dose of an agent or compound that binds to SMYD3 and regulates its activity depends on the symptoms, a typical dose ranges from about 0.1 mg to about 100 mg per day, preferably about 1.0 mg to about 50 mg per day and more preferably about 1.0 mg to about 20 mg per day, when administered orally to a normal adult (weight 60 kg).

When administering parenterally, in the form of an injection to a normal adult (weight 60 kg), although there are some differences according to the patient, target organ, symptoms and method of administration, it is convenient to intravenously inject a dose of about 0.01 mg to about 30 mg per day, preferably about 0.1 to about 20 mg per day and more preferably about 0.1 to about 10 mg per day. Also, in the case of other animals too, it is possible to administer an amount converted to 60 kgs of body-weight.

The present invention further provides a method for treating cancer in a subject, such as hepatocellular carcinoma, colorectal carcinoma, bladder cancer and breast cancer. Administration can be prophylactic or therapeutic to a subject at risk of (or susceptible to) a disorder or having a disorder associated with aberrant the methyltransferase activity of SMYD3. The method includes decreasing the function of SMYD3 in a suitable cancer cell. Function can be inhibited through the administration of an agent or compound obtained by a screening method of the present invention.

In another aspect, the present invention includes pharmaceutical, or therapeutic, compositions containing one or more therapeutic agents or compounds described herein. Alternatively, the present invention also provides use of one or more therapeutic agents or compounds described herein for manufacturing a pharmaceutical, or therapeutic, compositions for treating and/or preventing of cancer, more particularly hepatocellular carcinoma, colorectal carcinoma, bladder cancer and breast cancer. Pharmaceutical formulations may include those suitable for oral, rectal, nasal, topical (including buccal and sub-lingual), vaginal or parenteral (including intramuscular, sub-cutaneous and intravenous) administration, or for administration by inhalation or insufflation. The formulations may, where appropriate, be conveniently presented in discrete dosage units and may be prepared by any of the methods well known in the art of pharmacy. All such pharmacy methods include the steps of bringing into association the active compound with liquid carriers or finely divided solid carriers or both as needed and then, if necessary, shaping the product into the desired formulation.

Pharmaceutical formulations suitable for oral administration may conveniently be presented as discrete units, such as capsules, cachets or tablets, each containing a predetermined amount of the active ingredient; as a powder or granules; or as a solution, a suspension or as an emulsion. The active ingredient may also be presented as a bolus electuary or paste, and be in a pure form, i.e., without a carrier. Tablets and capsules for oral administration may contain conventional excipients such as binding agents, fillers, lubricants, disintegrant or wetting agents. A tablet may be made by compression or molding, optionally with one or more formulational ingredients. Compressed tablets may be prepared by compressing in a suitable machine the active ingredients in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may be coated according to methods well known in the art. Oral fluid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives. The tablets may optionally be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit dose or multi-dose containers, for example sealed ampoules and vials, and may be stored in a freeze-dried (lyophilized) condition requiring only the addition of the sterile liquid carrier, for example, saline, water-for-injection, immediately prior to use. Alternatively, the formulations may be presented for continuous infusion. Extemporaneous injection solutions and suspensions may be prepared from sterile powders, granules and tablets of the kind previously described.

Formulations for rectal administration may be presented as a suppository with the usual carriers such as cocoa butter or polyethylene glycol. Formulations for topical administration in the mouth, for example buccally or sublingually, include lozenges, comprising the active ingredient in a flavored base such as sucrose and acacia or tragacanth, and pastilles comprising the active ingredient in a base such as gelatin and glycerin or sucrose and acacia. For intra-nasal administration the compounds obtained by the invention may be used as a liquid spray or dispersible powder or in the form of drops. Drops may be formulated with an aqueous or non-aqueous base also comprising one or more dispersing agents, solubilizing agents or suspending agents. Liquid sprays are conveniently delivered from pressurized packs.

For administration by inhalation the compounds are conveniently delivered from an insufflator, nebulizer, pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the compounds may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflators.

When desired, the above described formulations, adapted to give sustained release of the active ingredient, may be employed. The pharmaceutical compositions may also contain other active ingredients such as antimicrobial agents, immunosuppressants or preservatives.

It should be understood that in addition to the ingredients particularly mentioned above, the formulations of this invention may include other agents conventional in the art having regard to the type of formulation in question, for example, those suitable for oral administration may include flavoring agents.

Preferred unit dosage formulations are those containing an effective dose, as recited below, or an appropriate fraction thereof, of the active ingredient.

For each of the aforementioned conditions, the compositions may be administered orally or via injection at a dose of from about 0.1 to about 250 mg/kg per day. The dose range for adult humans is generally from about 5 mg to about 17.5 g/day, preferably about 5 mg to about 10 g/day, and most preferably about 100 mg to about 3 g/day. Tablets or other unit dosage forms of presentation provided in discrete units may conveniently contain an amount which is effective at such dosage or as a multiple of the same, for instance, units containing about 5 mg to about 500 mg, usually from about 100 mg to about 500 mg.

The pharmaceutical composition preferably is administered orally or by injection (intravenous or subcutaneous), and the precise amount administered to a subject will be the responsibility of the attendant physician. However, the dose employed will depend upon a number of factors, including the age and sex of the subject, the precise disorder being treated, and its severity. Also the route of administration may vary depending upon the condition and its severity.

The following examples are merely illustrative and are not intended to limit the scope of the present invention. While aspects of the present invention are described in the following examples, those skilled in the art will recognize that other methods and materials similar or equivalent to those described herein can be used in the practice or testing of the present invention.

EXAMPLES

Materials and Methods:
Reagents:
Anti-RB (IF8), anti-phospho RB (Ser 807/811, sc-16670), and anti-phospho RB (Thr 821/826) antibodies were purchased from Santa Cruz Biotechnology, anti-Flag antibody from SIGMA, and anti-pan-methyl lysine antibody (ab7315) was from Abcam Ltd. Recombinant SMYD3 protein or synthetic RB1 peptides (residues 820-828) containing di- or tri-methylated lysine 824 were inoculated into rabbits (SIGMA-ALDRICH, St. Louis, Mo.), and polyclonal antibodies were purified from sera of the immunized rabbits. Recombinant C-terminal GST-RB1 and full-length GST-p53 proteins were from Santa Cruz Biotechnology, His-conjugated C-terminal RB1, CDK2/cyclin E and CDK6/cyclinD3 proteins were from Upstate Biotechnology, full-length recombinant RB protein (3108) was from QED Bioscience. S-(5'-Adenosyl)-L-homocysteine hydrolase (SAHH) was obtained from SIGMA.

In Vitro Methyltransferase and Kinase Assays:
293T cells were transfected with plasmid expressing Flag-tagged wild-type SMYD3 (p3XFLAG-CMV-SMYD3), mutant SMYD3 (p3XFLAG-CMV-SMYD3ΔEEL), and purified tagged-SMYD3 protein by immunoprecipitation with anti-Flag antibody. Recombinant SMYD3 protein was prepared in Sf9 cells using Baculovirus system (Clontech). In vitro HMTase assay was performed with a slight modification as described elsewhere (Strahl, B. D., et al. Proc Natl Acad Sci USA 96, 14967-72 (1999)). Briefly, immunoprecipitated or recombinant SMYD3 protein was mixed with 1 μg of recombinant histone H3, RB1, or p53 protein in the presence of 2 μCi of [methyl-$^3$H]-labeled S-adenosyl-L-methionine (SAM, Amersham Biosciences) as methyl donor in methyltransferase buffer (50 mM Tris-HCl pH 8.5, 100 mM NaCl, 10 mM DTT). The reaction mixture was incubated for 1 hr at 30° C. Proteins were separated in SDS-PAGE, and labeled proteins were detected by fluorography. In vitro kinase assays of CDK2/cyclinE and CDK6/cyclinD3 were carried out according to the manufacture's protocol (Upstate Biotechnology). Both non-methylated and methylated RB1 (#12-439, Upstate Biotechnology) were used as the reaction substrate.

In Vivo Methylation Assay:
To measure methylated RB1 in vivo, in vivo labeling of RB1 was carried out with [methyl-$^3$H]-labeled S-adenosyl-L-methionine in cultured cells, according to the method described by Liu and Dreyfuss (Liu, Q. & Dreyfuss, G. Mol Cell Biol 15, 2800-8 (1995)) with slight modification. HEK293 cells were incubated with 100 μg/ml of cycloheximide and 40 μg/ml of chloramphenicol at 37° C. for 30 min, when the medium was then replaced by medium containing 10 μCi/ml of L-[methyl-$^3$H] methionine and the protein synthesis inhibitors without unlabeled methionine, and maintained for an additional 3 h. The whole cell lysates were subjected to immunoprecipitation with anti-RB antibody (IF8; Santa Cruz Biotechnology). The immunoprecipitated RB1 protein was separated on SDS-PAGE, and subsequently transferred to a nitrocellulose membrane, which was analyzed by BAS imaging system (BAS-TR2040, FUJI) or immunoblot analysis.

Immunocytochemical Staining:
Cultured cells on chamber slides were fixed with PBS containing 4% paraformaldehyde for 15 min, then rendered permeable with PBS containing 0.1% Triton X-100 for 2.5 min at room temperature. The cells were covered with 2% BSA in PBS for 24 h at 4° C. to block non-specific hybridization, and then incubated with anti-SMYD3 antibody, anti-RB [IF8] antibody and anti-phospho RB (Thr 821/826) antibody as the first antibody. As secondary antibody, fluorescent substrate-conjugated anti-rabbit or anti-mouse IgG (Molecular probes) were used; nuclei were counter-stained with 4', 6-diamidino-2-phenylindole dihydrochloride (DAPI). Fluorescent images were obtained with TCS-SP2 confocal microscope (Leica).

Luciferase Assay:

Luciferase assays were carried out using a Dual-Luciferase Reporter Assay System according to the manufacturer's instructions (Promega).

Cell Lines and Tissue Specimens:

Human embryonic kidney 293 (HEK293), HEK293T, and HEK293F cells were purchased from IWAKI. A human hepatoma cell line HepG2, and HCT116 and SW480 human colon cancer lines were obtained from the American Type Culture Collection (ATCC). A human HCC cell line SNU423 was a gift from the Korea cell-line bank. T47D and MCF7 breast cancer cell lines were kindly provided from the cancer institute of the Japanese foundation for cancer research. All cell lines were grown in monolayers in appropriate media. Primary breast cancer tissues were obtained with informed consent from patients (Hamamoto, R. et al. *Cancer Sci* 97, 113-118 (2006)).

Preparation of Plasmids:

Preparation of C-terminal FLAG-tagged SMYD3 was described previously (Hamamoto, R. et al. *Nat Cell Biol* 6, 731-740 (2004)). We additionally prepared plasmids expressing N-terminal HA-tagged, or N-terminal 3×FLAG-tagged SMYD3 by cloning various PCR products containing either wild-type or deleted forms of SMYD3 cDNA into an appropriate site of pCMV-HA (Clontech) or p3×FLAG-CMV14 (Sigma) vector. Primers used for wild-type plasmids were 5'-AAGCTTGCGGCCGCGATGGAGCCGCT-GAAGGTGGAAAAG-3' (SEQ ID NO: 5), and 5'-GGTAC-CTCTAGATTAGGATGCTCTGATGTTGGCGTC-3' (SEQ ID NO: 6), and those used for mutants (FLAG-SMYD3-ΔN44, -ΔN99, -ΔN244, and -ΔN34) were 5'-GGGGTACCT-TAGGATGCTCTGATGTTGGCGTC-3' (SEQ ID NO: 7) and 5'-CGGAATTCTGGCGCGATGGAGCCGCT-GAAGGTGGAAAAG-3' (SEQ ID NO: 8), 5'-CGGAAT-TCTGACTCCGTTCGACTTCTTGGCAG-3' (SEQ ID NO: 9), 5'-CGGAATTCTCGGAAGCAGCTGAGGGAC-CAGTACTGC-3' (SEQ ID NO: 10), or 5'-CGGAATTCAC-CCTTGGCGTACACGGTGTGCAAGG-3' (SEQ ID NO: 11), respectively. Mutant plasmids expressing substitution(s) at glycine 15, 17, or 27 were prepared using QuikChange II XL site-directed mutagenesis Kit according to the supplier's protocol (Stratagene, Calif., USA).

Western Blot Analysis:

A polyclonal antibody to SMYD3 was purified from sera of rabbits immunized with a recombinant His-tagged SMYD3 protein produced in *E. coli* as described elsewhere. Proteins were separated by 10% SDS-PAGE and immunoblotted with anti-SMYD3, anti-HA (Sigma), anti-FLAG (Sigma), anti-GST (Pharmingen), or anti-β-actin (Sigma) antibody. HRP-conjugated anti-rabbit IgG, anti-mouse IgG (Amersham Biosciences), or anti-goat IgG (Santa Cruz) antibody served as the secondary antibody for the ECL Detection System (Amersham).

Determination of Cleavage Site:

C-terminal-FLAG-tagged SMYD3 was expressed exogenously in 293F cells. Immunoprecipitated SMYD3 protein with anti-FLAG antibody from the cells was separated on duplicated SDS-PAGE gels, and transferred to a nitrocellulose membrane and a sequence grade PVDF membrane. The nitrocellulose membrane was used for immunoblot analysis with anti-FLAG antibody to detect two forms of SMYD3 protein. After staining of the PVDF membrane with CBB solution without acetic acid (0.025% CBB in 40% methanol), we excised the band corresponding the short form of SMYD3 and subjected to amino acid sequence. The amino acid sequence of the protein was determined by Edman amino acid sequence method (Shimadzu Biotechnologies, Tokyo, Japan).

In Vitro Histone Methyltransferase (HMTase) Assay:

FLAG-tagged SMYD3 was purified from 293T cells expressing wild-type (p3XFLAG-CMV-SMYD3) or mutant SMYD3 (p3XFLAG-ΔN34, -ΔN44, -SETNm1, -SETNm2 and -SETNm3) by immunoprecipitation with anti-FLAG antibody. GST-fused SMYD3 proteins were purified from bacterial cells expressing wild-type (GST-SMYD3-wt) or mutant SMYD3 constructs (GST-SMYD3-ΔN9, -ΔN19, -ΔN29, -ΔN44, -ΔN74). In vitro HMTase assay was performed as described elsewhere (Hamamoto, R. et al. *Nat Cell Biol* 6, 731-740 (2004)). 3H-radioactivity was measured by liquid scintillation counter.

Example 1

RB1 as a Substrate for SMYD3

Since two recent reports showed that a histone H3-K4 methyltransferase SET7/9 catalyzes TAF10 and p53 as a substrates (Chuikov, S. et al., *Nature* 432, 353-60 (2004)), the present inventors searched for additional substrates for SMYD3 (GenBank Accession NO. AB057595; SEQ ID NO; 1, 2) other than histone H3. Because they are well known regulators of cell cycle progression, p53 and RB1 were first tested (GenBank Accession NO. NM_000321; SEQ ID NO; 3, 4) as candidate substrates. In the course of investigation, recombinant histone H3, wild-type p53, and C-terminal region of RB1 (codons 769-921) were incubated in the presence of $^3$H-labeled SAM, a methyl donor, together with immunoprecipitated SMYD3 protein from 293T cells. Subsequent PAGE and autoradiography showed bands corresponding methylated histone H3, which is consistent with the finding that SMYD3 methylate histone H3. Interestingly, bands corresponding to methylated RB1 were also detected; however, no bands corresponding to methylated p53 were detected (FIG. 1*a*). The methyltransferase (MTase) activity to histone H3 and the C-terminal RB1 was further measured using recombinant SMYD3 protein. The results revealed a dose-dependent increase of MTase activity on both substrates (FIG. 1*b*). Notably, the MTase activity was higher to the C-terminal RB1 compared to histone H3. It was further discovered that SET7/9 also has a methyltransferase activity to RB1 (data not shown). In addition, SMYD3 methylated full length of RB1 (FIG. 1*c*), suggesting that RB1 is methylated in vitro by SMYD3 as well as SET7/9, two histone H3-K4 methyltransferases.

Example 2

The Methyltransferase Activity of SMYD3 on RB1 Proteins

Figure 2:
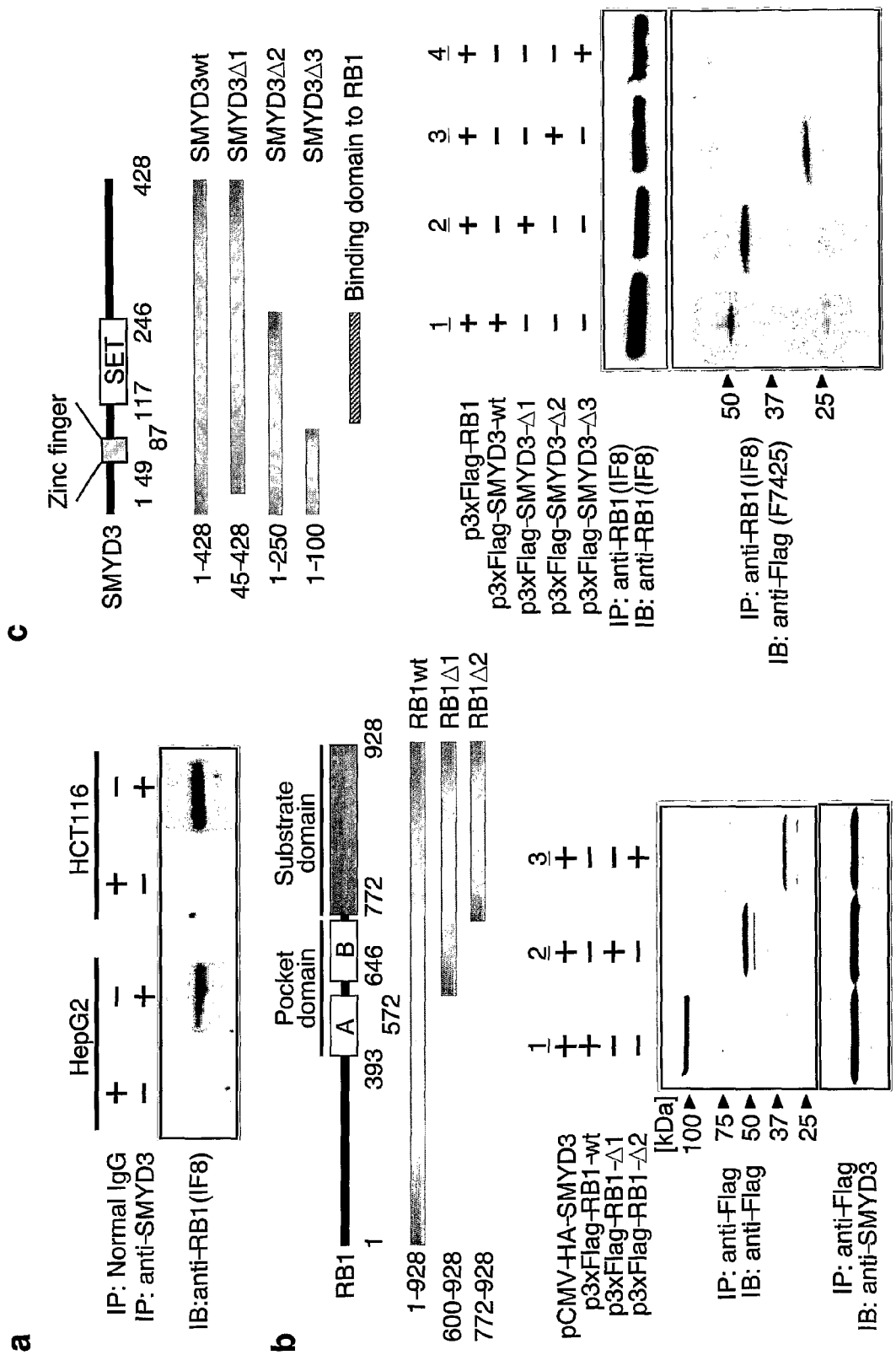
FIG. 2 depicts the association between SMYD3 and RB1 in vivo. Part a depicts the results of an immunoassay. Specifically, immunoprecipitants from lysates of HepG2 or HCT116 cells using anti-SMYD3 antibody were immunoblotted with anti-RB1 antibody. Part b depicts the interaction between wild type and deleted forms of RB1 (RB1Δ1 and RB1Δ2) and SMYD3 in HEK293 cells (Lower). Conserved regions and expression constructs of RB1 are shown in the upper panel. Part c depicts the region of SMYD3 responsible for the interaction with RB1. Conserved regions and expression constructs of SMYD3 are illustrated in the upper panel. Part d depicts the in vitro methyltransferase activity of SMYD3 to histone H3 with/without recombinant RB1. Methylation of histone H3 was unaffected by RB1 (upper panel). Equal amounts of recombinant human histone H3 protein were used as substrate (lower panel). Part e depicts the in vitro analysis of histone H4-K20 methylation. Immunoprecipitated or recombinant SMYD3 protein was incubated with recombinant human histone H4 as substrate. Immunoprecipitated Suv4-20h2 protein served as a positive control. Methylated H4-K20 was detected with anti-tri-methyl H4-K20 antibody.

To investigate a possible association between SMYD3 and RB1 proteins, proteins extracted from HepG2 or HCT116 cells were immunoprecipitated with anti-SMYD3 antibody. As expected, bands corresponding to RB1 protein were observed by immunoblot analysis with anti-RB1 antibody (FIG. 2*a*). To determine the region of RB1 responsible for the association, Flag-tagged wild type or mutant RB1 protein were expressed together with an HA-tagged SMYD3 in HEK293 cells, and immunoprecipitation was carried out with an anti-Flag antibody. In line with the methylation of C-terminal RB1 protein, the C-terminal substrate domain (codons 772-928) interacted with SMYD3 (FIG. 2*b*). To determine the region of SMYD3 responsible for the binding with RB1, plasmids expressing wild type and various forms of mutant SMYD3 were used. Although wild type, and Δ1-(codons 45-428) and Δ2-forms (codons 1-250) of mutant SMYD3 interacted with Flag-tagged RB 1, Δ3-form lacking the SET domain (codons 1-100) did not interact with RB1, suggesting that the SET domain is essential for the association (FIG. 2c). An earlier report showed that histone H3-K9 methyltransferase SUV39H1 associates with RB and HP1, and the complex plays a role in transcriptional suppression of cyclin E (Nielsen, S. J. et al. Nature 412, 561-565 (2001)). Additionally, a recent study revealed that activity of histone H4-K20 methyltransferases, Suv4-20h1 and Suv4-20h2, was markedly enhanced through an interaction with RB1 (Gonzalo, S. et al. Nat Cell Biol 7, 420-428 (2005)). Therefore, the present inventors tested whether RB1 enhances H3-K4 methyltransferase activity of SMYD3 or not. As a result, SMYD3-mediated methylation of histone H3 was not affected by RB1 (FIG. 2d). Notably, SMYD3 did not show methyltransferase activity to H3-K910 or H4-K20 (FIG. 2e). This data strengthens the H3-K4-specific HMT (histone methyltransferase) activity of SMYD3, and suggested that RB1 plays a role for histone modification in an HMT-dependent fashion.

Example 3

Identification of the Methylation Substrate Domain of RB1

Figure 3:
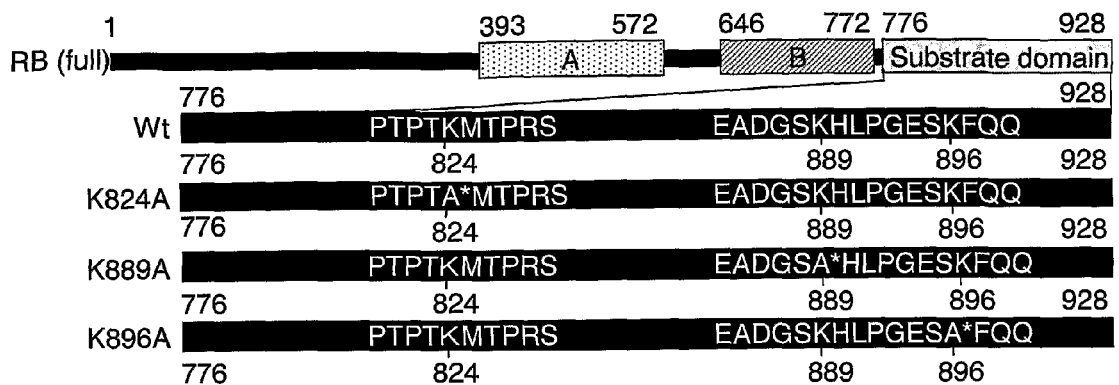
FIG. 3 depicts the methylation of K824 in the C-terminal region of RB1. Part a (SEQ ID NOS:29-33) is a schematic representation of the conserved domains of RB1, and wild type and mutated forms of C-terminal RB1 protein (K824A, K889A, and K896A). Part b depicts the detection by autoradiography of methylated C-terminal RB1 separated on SDS-PAGE. Part c depicts MTase activity measured by liquid scintillation counter. Part d depicts the in vitro methylation of recombinant wild-type and mutant forms of RB1 proteins, including K791A, K814A, K824A, K791/K824A, and K814/K824A. RB1 was incubated with recombinant SMYD3 protein in the presence of $^3$H-labeled SAM. Methylated RB1 was separated on SDS-PAGE and detected by fluorogram. Part e depicts methylated RB1 measured by liquid scintillation counter. Part f depicts the di- and tri-methylation of RB1 lysine 824 by SMYD3. Methylated wild-type RB1 protein in the presence or absence of SMYD3 was detected by $^3$H-BAS imaging system (upper panel). Western-blot analysis of the RB1 protein using anti-di-methylated lysine 824 (second panel) or anti-tri-methylated lysine 824 (third panel) antibodies. Total amount of RB1 was quantified with anti-RB1 antibody (fourth panel).
Figure 3:
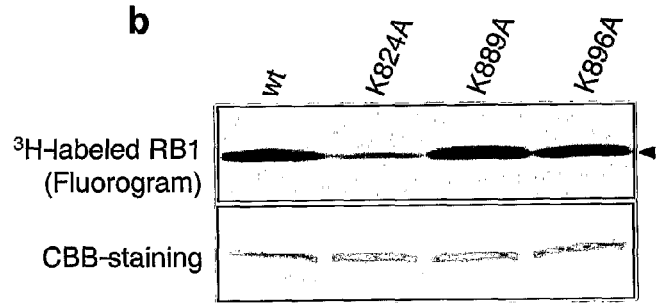
Figure 3:
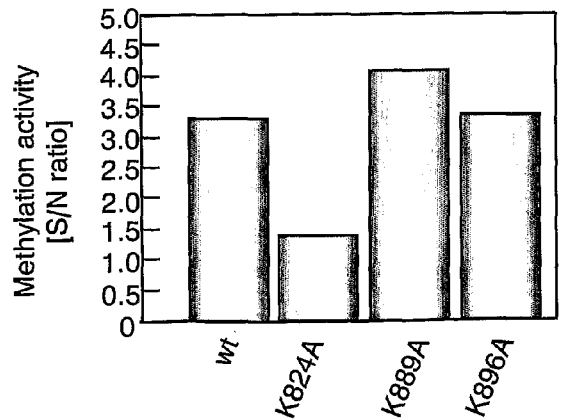

To determine the residue(s) responsible for the methylation of the substrate domain of RB1, conserved amino acid sequences in the substrates of SET7/9 methyltransferases were compared. Since the methylated lysines were preceded by either serine or threonine, the present inventors focused on lysine 824, lysine 889, and lysine 896 as candidates. Recombinant proteins, of wild type and three forms of mutant substrate domain of RB1, were prepared (FIG. 3a). Compared to the wild type protein, the K889A and K896A mutants were methylated at similar levels by SMYD3 (FIG. 3b, c); however, methylation of K824A was significantly decreased (FIG. 3b, c). Additionally, because replacement of K824A did not completely diminish methylation of RB1 protein, the methylation of lysine 791 and lysine 814, both of which are preceded by tyrosine, were examined. Two mutant RB1 proteins, K791A and K814A, showed similar levels of methylation to wild type-RB1 (FIG. 3d, e). Furthermore, two forms of double-mutant RB1, K791A/K824A and K814A/K824A, showed equivalent levels of methylation to the K824A protein. Hence, the present inventors concluded that that lysine 824 is a major target residue for the methylation. To confirm the methylation of lysine 824, methylated RB1-specific antibodies that recognize di- or tri-methylated lysine 824 were prepared. In accordance with the methylation of wild-type RB1 protein, the antibodies detected di- and tri-methylated RB1 protein in immunoblot analysis (FIG. 3f) as similar to that SMYD3 exerts di- and tri-methylation of histone H3 lysine 4 (Hamamoto, R. et al. Nat Cell Biol 6, 731-740 (2004)). Although the methylated lysines in the substrates of SET7/9 including H3-K4, TAF10, and p53, were preceded by two conserved peptides, R/K at the -2 position of lysine and S/T at the -1 position, the lysine 824 was preceded by P at the -2, and T at the -1. Because RB1 is methylated by SMYD3 as well as SET7/9, R/K at the -2 may not be essential but S/T at the -1 is indispensable for the methylation by SMYD3 or SET7/9.

Example 4

In Vivo Methylation Assays

Figure 4:
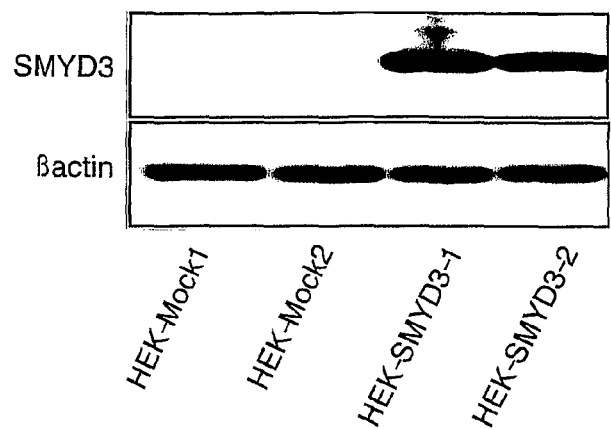
FIG. 4 depicts the methylation of RB1 by SMYD3 in vivo. Part a depicts the expression of SMYD3 in HEK-SMYD3 (HEK-SMYD3-1 and -2) cells and HEK-Mock (HEK-Mock-1 and -2) cells (upper panel). Part b depicts the detection of methylated RB1 in vivo by radiogram using immunoprecipitants from HEK-SMYD3 and HEK-Mock cells with anti-RB1 antibody (upper panel). The amount of immunoprecipitated RB1 was unchanged. Cells were treated with $^3$H-labeled SAM in the presence of protein synthesis inhibitor. The amount of immunoprecipitated RB1 was unchanged (lower panel). Part c depicts the results of a western blot analyzing the methylation of the immunoprecipitated RB1 using anti-pan-methyl lysine, anti-di-methyl lysine 824 and anti-tri-methyl lysine 824 antibodies. Parts d-k depict the results of immunocytochemical staining of HEK293-SMYD3 cells with anti-di-methyl lysine 824 (d) or anti-tri-methyl lysine 824 (h) antibodies. Parts e and i depict the expression of SMYD3 examined using anti-SMYD3 antibody. Parts f and j depict the results of nuclear staining with DAPI. Parts g and k constitute merged images of d-f (g) or h-j (k). Cells abundantly expressing SMYD3 showed enhanced di- and tri-methylation of RB1 Lys 824 in vivo.
Figure 4:
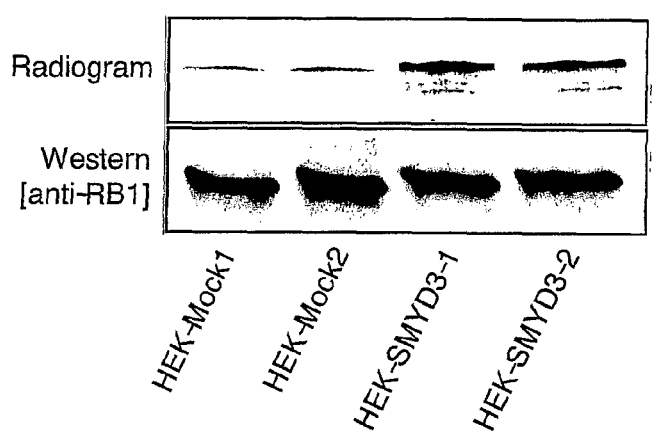
Figure 4:
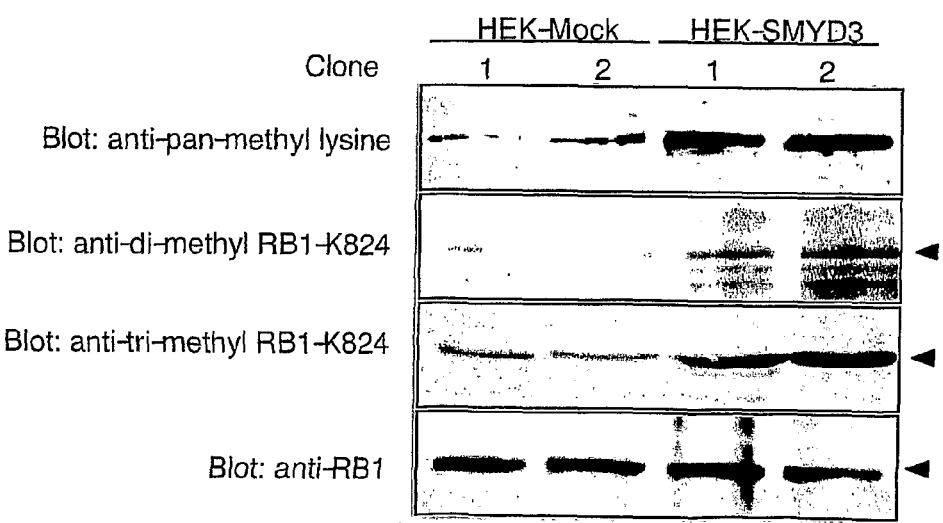

To further examine methylation of RB1 by SMYD3 in vivo, in vivo methylation assays were carried out (Liu, Q. & Dreyfuss, G. Mol Cell Biol 15, 2800-8 (1995)) using HEK293 cells that do not express SMYD3. HEK293 cell lines expressing SMYD3 (HEK-SMYD3-1 and -2) (FIG. 4a) were established and incubated the cells with L-[methyl-$^3$H] methionine in the presence of protein synthesis inhibitors. Extracts from the cells were then immunopurified with anti-RB1 monoclonal antibody, and the immunoprecipitated proteins were analyzed by SDS-PAGE and subsequent autoradiography. Compared to mock-transfected HEK293 cells (HEK-Mock-1 and -2), extracts from HEK-SMYD3 (HEK-SMYD3-1 and -2) cells showed significantly stronger bands corresponding to methylated RB1. Amount of immunoprecipitated RB1 was unchanged among the cell lines (FIG. 4b). Consistently, an increase in methylated RB1 was observed in HEK-SMYD3 cells as compared to HEK-Mock cells by western blot analysis using anti-pan-methyl-lysine, anti-dimethylated RB1-lysine 824, or anti-tri-methylated RB1-lysine 824 antibodies (FIG. 4c). Immunocytochemical staining of HEK-SMYD3 cells showed that cells expressing abundant amount of SMYD3 were more strongly stained with anti-di-methylated or anti-tri-methylated RB1-lysine 824 antibodies (FIG. 4d-g, 4h-k, respectively) than those expressing a smaller amount of SMYD3. This data corroborates the methylation of RB1-lysine 824 by SMYD3 in vivo.

Example 5

In Vivo Phosphorylation Assays

Figure 5:
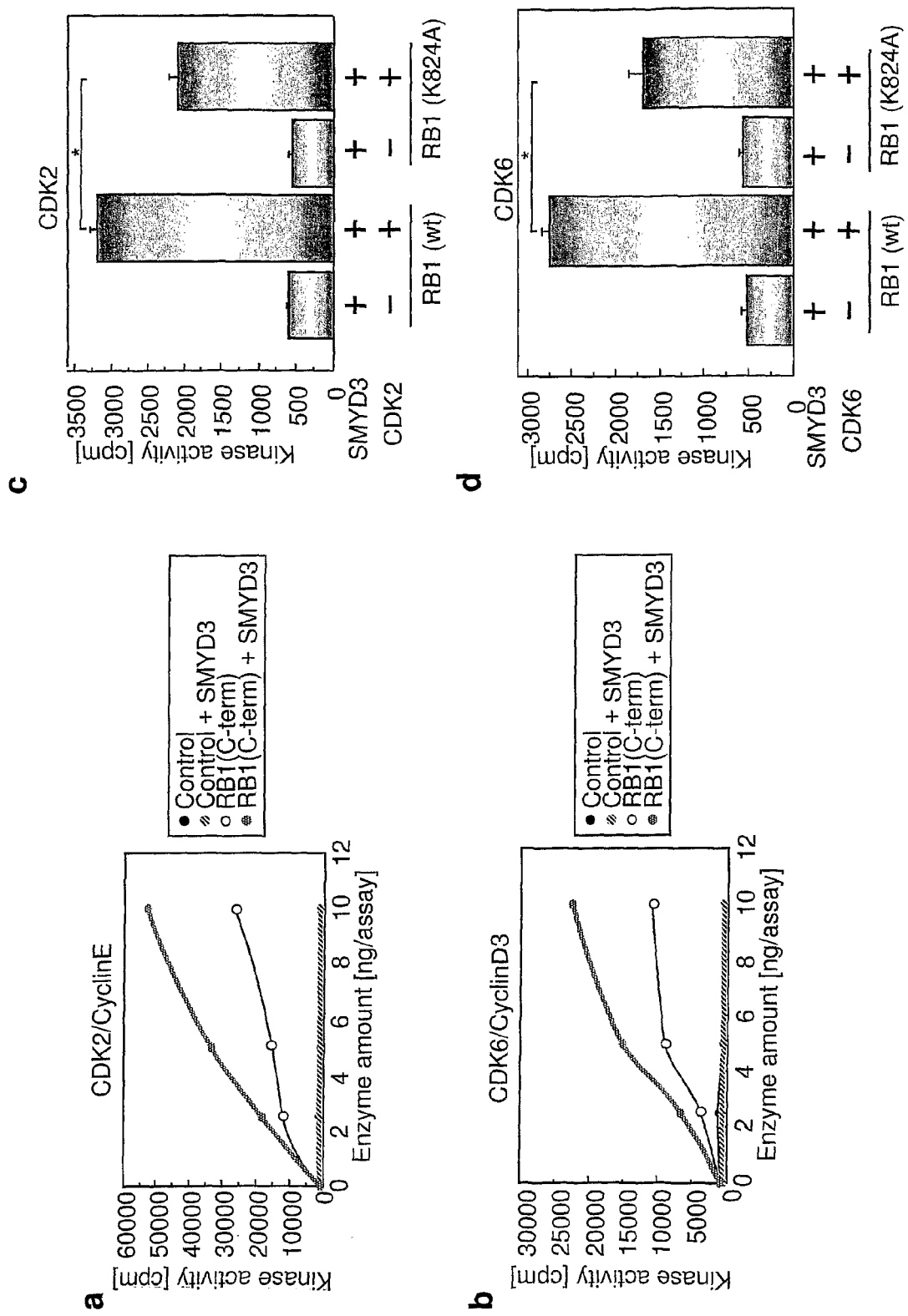
FIG. 5 depicts the enhanced phosphorylation of RB1 by SMYD3 Part a depicts the in vitro phosphorylation of C-terminal RB1 by CDK2/cyclin E in the presence or absence of SMYD3. SMYD3 alone failed to increase the phosphorylation. Part b depicts the in vitro phosphorylation of C-terminal RB1 by CDK6/cyclinD3 in the presence or absence of SMYD3. Enhancement of RB1 phosphorylation by SMYD3 was repressed using K824A substituted RB1. Part c depicts the in vitro phosphorylation of C-terminal RB1 by CDK2/cyclin E comparing wild-type (Wt) and K824A mutant (K824A) as a substrate. Part d depicts the in vitro phosphorylation of C-terminal RB1 by CDK6/cyclin D3 comparing Wt and K824A as a substrate. Part e depicts the increased Ser807/811, and Thr821/826 phosphorylation by CDK2/cyclin E or CDK6/cyclinD3 complexes in the presence of SMYD3. Part f depicts the elevated Ser807/811 and Thr821/826 phosphorylation in HEK-SMYD3 cells as compared to HEK-Mock cells. Immunocytochemical staining of HEK293 cells expressing exogenous SMYD3. Part g depicts the results of staining phosphorylated RB1 in the cells with anti-phospho RB1 (Thr 821/826) antibody. Part h depicts the expression of SMYD3 in the cells. Part i depicts the results of nuclear staining with DAPI. Part j constitutes a merged image of g-i. Cells expressing SMYD3 showed enhanced phosphorylation of Thr821/826 in vivo.

The lysine 824 of RB1 is located between threonine $821^{st}$ and $826^{th}$; residues phosphorylated by CDK/cyclin complexes, and that regulate the interaction between RB1 and E2F through the conformational change of central pocket domain. To examine the effect of RB1 methylation on the phosphorylation of these surrounding threonines, in vivo phosphorylation assays were carried out using methylated or unmethylated RB1 protein. Recombinant C-terminal RB1 was incubated with $^3$H-labeled SAM in the presence or absence of SMYD3, and then mixed with $^{32}$P-γATP in combination with either recombinant CDK2/CyclinE or CDK6/CyclinD3. Methylation and phosphorylation of the recombinant RB1 was measured simultaneously by liquid scintillation counter. The C-terminal RB1 protein incorporated four to six fold higher amount of $^3$H-labeled methyl donor in the presence of SMYD3 than the absence of SMYD3 (data not shown). Importantly, SMYD3 enhanced the phosphorylation of RB1 by CDK2/CyclinE complex in a dose-dependent manner, while SMYD3 alone did not increase the phosphorylation (FIG. 5a). In addition, it was discovered that phosphorylation of RB1 is augmented by CDK6/CyclinD3 in the presence of SMYD3 compared to the absence of SMYD3 (FIG. 5b). However, phosphorylation of the K824A mutant RB1 by CDK2/Cyclin E or CDK6/Cyclin D3 was significantly suppressed, compared to wild type RB1 (FIG. 5c, d, respectively). This data suggests that phosphorylation of RB1 is enhanced through the methylation of lysine 824 by SMYD3. Additional immunoblot analysis using anti-phosphorylated RB1 antibody revealed that the phosphorylation of threonine 821/826 was induced by SMYD3. Interestingly, phosphorylation of serine 807/811 was also enhanced by SMYD3 (FIG. 5e). Therefore, methylation of lysine 824 increase the phosphorylation of serine 807/811, or additional methylated residue(s) may enhance the phosphorylation.

Figure 6:
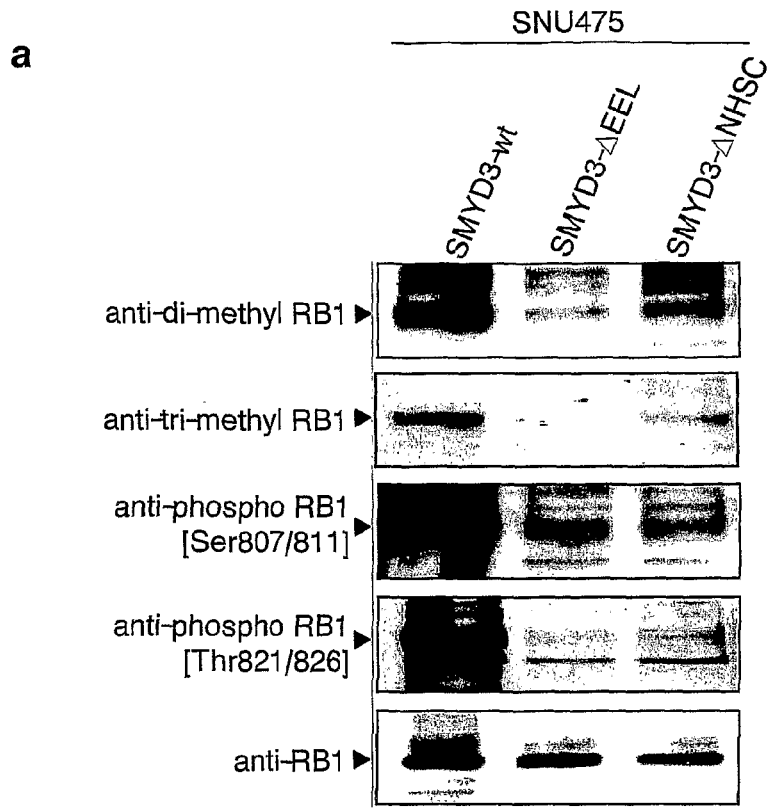
FIG. 6 depicts the methylation and enhanced phosphorylation of RB1 by SMYD3. In part a, RB1 protein was immunoprecipitated from SNU475 cells transfected with wild type (p3×Flag-SMYD3) or mutant SMYD3 plasmids (p3×Flag-SMYD3ΔEEL and p3×Flag-SMYD3ΔNHSC). Western blot analysis was carried out with anti-di-methylated lysine 824 (top panel), anti-tri-methylated lysine 824 (second panel), anti-phospho-serines 807/811 (third panel), or anti-phospho-threonines 821/824 (fourth panel) antibodies using the precipitants. Immunoblot analysis with anti-RB1 antibody served for a quantity control (bottom panel). Part b depicts the di- and tri-methylation of lysine 824, and phosphorylation of Ser807/811 and Thr821/826 in two breast cancer tissues. Western blot analysis was carried out with anti-di-methylated lysine 824, anti-tri-methylated lysine 824, anti-phospho RB (Ser807/811), or anti-phospho RB (Thr821/824) antibodies.
Figure 6:
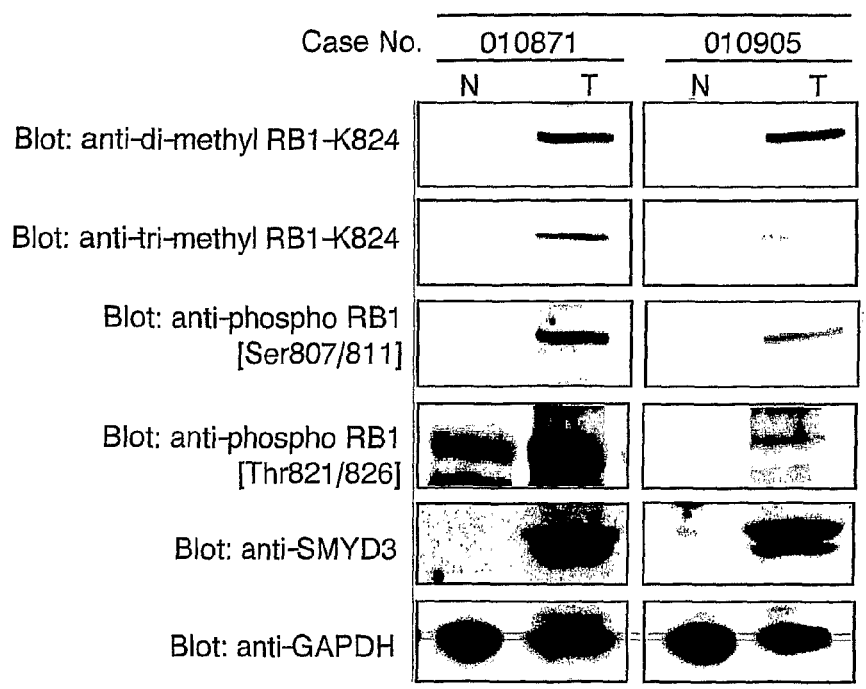
Figure 7:
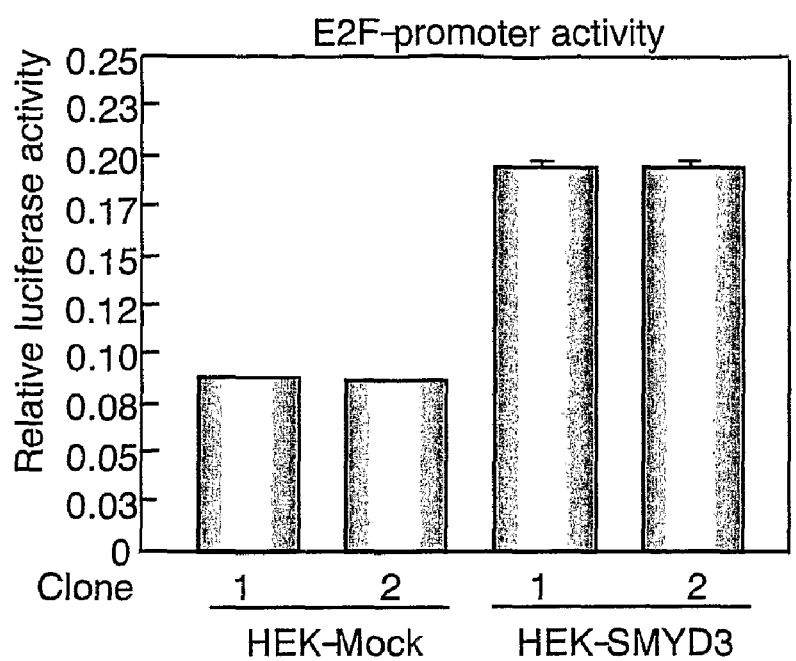
FIG. 7 depicts the augmented E2F-transcriptional activity in HEK-SMYD3 cells. Luciferase activity was measured 24 h after transfection with E2F-luciferase vector in HEK-SMYD3 and HEK-Mock cells. Immunocytochemical staining of HEK293 cells expressing exogenous SMYD3. Phosphorylated RB1 in the cells was stained with anti-phospho RB1 (Thr 821/826) antibody. Part h depicts the expression of SMYD3 in the cells. Part i depicts the results of nuclear staining with DAPI. Part j constitutes a merged image of a-c. Cells expressing SMYD3 showed enhanced phosphorylation of Thr821/826 in vivo.

To investigate enhanced phosphorylation of RB1 in vivo, western blot analysis was carried out with anti-phosphorylated RB1 antibody using extracts from HEK-SMYD3 and HEK-Mock cells. Consistent with the enhanced phosphorylation of RB1 protein in vitro, elevated phosphorylation of both serine 807/811 and threonine 821/826 was detected in HEK-SMYD cells as compared to the control cells (FIG. 5f). Immunocytochemical staining using anti-phosphorylated threonine 821/826 antibody and anti-SMYD3 antibody revealed that cells expressing SMYD3 were more strongly stained with anti-phosphorylated threonine 821/826 antibody than cells that do not express SMYD3 (FIG. 5g-j). In addition, exogenous expression of wild type SMYD3 augmented di- and tri-methylation of RB1 lysine 824 in SNU475 cells compared to that of mutant SMYD3 (SMYD3-ΔEEL or SMYD3-ΔNHSC) that lacks methyltransferase activity (Hamamoto, R. et al. Nat Cell Biol 6, 731-40 (2004)). Correlated with the methylation of RB1 lysine 824, we observed remarkable and moderate increase of phosphorylation at threonines 821/826 and serines 807/811, respectively, in the cells (FIG. 6a). Importantly, western blot analysis showed enhanced methylation of RB1 lysine 824 together with increased phosphorylation of serines 807/811 and threonines 821/826 in breast cancer tissues that express augmented SMYD3 compared to corresponding non-cancerous mammary tissues (FIG. 6b). This data recapitulated the enhanced phosphorylation of serine 807/811 and threonine 821/826 by SMYD3 in vivo. Since phosphorylation of RB1 modulates the pocket domain leading to dissociation of E2F from RB1, reporter activity of E2F-mediated transcription was compared in the HEK-SMYD3 cells using the Mercury™ cell cycle profiling system. Compared with HEK-Mock cells, HEK-SMYD3 cells showed elevated E2F transcriptional activity (FIG. 7). This data indicates that SMYD3 enhances the phosphorylation of RB1 through methylation of the lysine 824, which leads to elevated E2F transcriptional activity.

Example 6

A Cleaved Form of SMYD3 Protein in Human Cancer Cells

Figure 8:
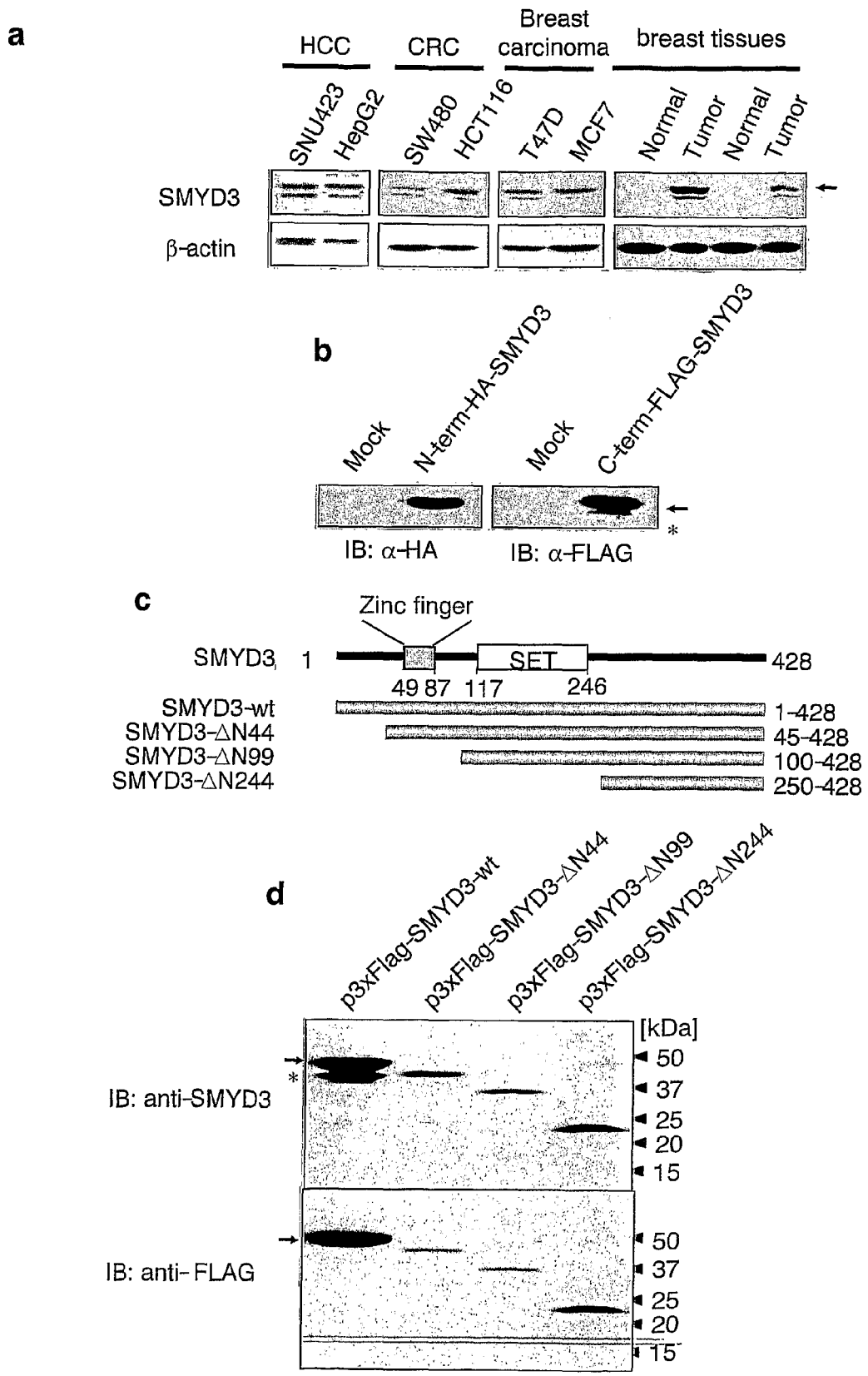
FIG. 8 Expression patter of SMYD3 protein. Part a depicts Expression of SMYD3 protein in human cancer cell lines and tissues. Western blot analysis was carried out using anti-SMYD3 antibody. Expression of β-actin served as a quantitative control. Part b depicts immunoblot analysis of HA-tagged SMYD3 (left panel) and FLAG-tagged (right panel). Western blot analysis was carried out with anti-HA antibody or anti-FLAG antibody using extracts from cells expressing HA-tagged SMYD3 in the N-terminal region or Flag-tagged SMYD3 in the C-terminal region, respectively. Part c depicts schematic presentation of deleted forms of SMYD3. Plasmids expressing a series of FLAG-tagged SMYD3 in its N-terminal region were transfected into HEK93 cells that do not express endogenous SMYD3. Part d depicts western blot analysis of extracts from the cells was performed using anti-SMYD3 antibody (upper panel) or anti-FLAG antibody (lower panel). Arrows indicate full-length SMYD3 protein, and an asterisk corresponds to a cleaved form of SMYD3.

We showed in our earlier studies that expression levels of SMYD3 protein is elevated in human hepatocellular carcinoma (HCC), colorectal carcinoma (CRC), and breast cancer (Hamamoto, R. et al. *Nat Cell Biol* 6, 731-740 (2004), Hamamoto, R. et al. *Cancer Sci* 97, 113-118 (2006)). Interestingly, western blot analysis with anti-SMYD3 antibody showed two bands of 45-kDa and 42-kDa in all breast cancer tissues examined, but it detected neither of the two bands in normal mammary gland. Both of 45-kDa and 42-kDa bands were observed in HCC, CRC, and breast cancer cell lines (FIG. 8a) and normal testis (data not shown). The predicted molecular weight of SMYD3 was 45 kDa, and we did not find any altered forms of SMYD3 transcript in our RT-PCR analysis. Therefore, we hypothesized that the 42-kDa band might result from cleavage of full-length SMYD3 protein. To examine the cleavage of SMYD3, we prepared plasmids expressing N-terminal HA-tagged SMYD3 or C-terminal FLAG-tagged SMYD3. Extracts of HEK293 cells expressing HA-tagged or FLAG-tagged SMYD3 protein were used for immunoblot analysis with anti-HA or anti-FLAG antibodies, respectively. As a result, we obtained 46-kDa band of corresponding to the N-terminal HA-tagged protein with anti-HA antibody. While we found two bands 46-kDa and 43-kDa proteins with anti-FLAG antibody (FIG. 8b). This result suggested that the full length protein was cleaved in its N-terminal region. To investigate the cleavage site, we expressed exogenously wild-type and deletion mutants of SMYD3 containing N-terminal 3XFLAG-tag in HEK293 cells that do not express endogenous SMYD3 (FIG. 8c). Consistent the data of FIG. 8b, western blot analysis with anti-FLAG antibody showed a band corresponding to the 48-kDa FLAG-tagged full-length protein alone in the cells expressing wild-type SMYD3. However, analysis with anti-SMYD3 antibody using the same extract detected two bands corresponding to the 48-kDa FLAG-tagged SMYD3 and 42-kDa protein. Western blot analysis with anti-SMYD3 antibody using extracts from cells expressing N-terminal deleted forms of SMYD3 (FLAG-SMYD3-ΔN44, -ΔN99, and -ΔN244) showed single bands. These data suggested that the cleavage site of SMYD3 localized between codons 1 and 45.

Example 7

Determination of Cleavage Site of SMYD3 Protein

Figure 9:
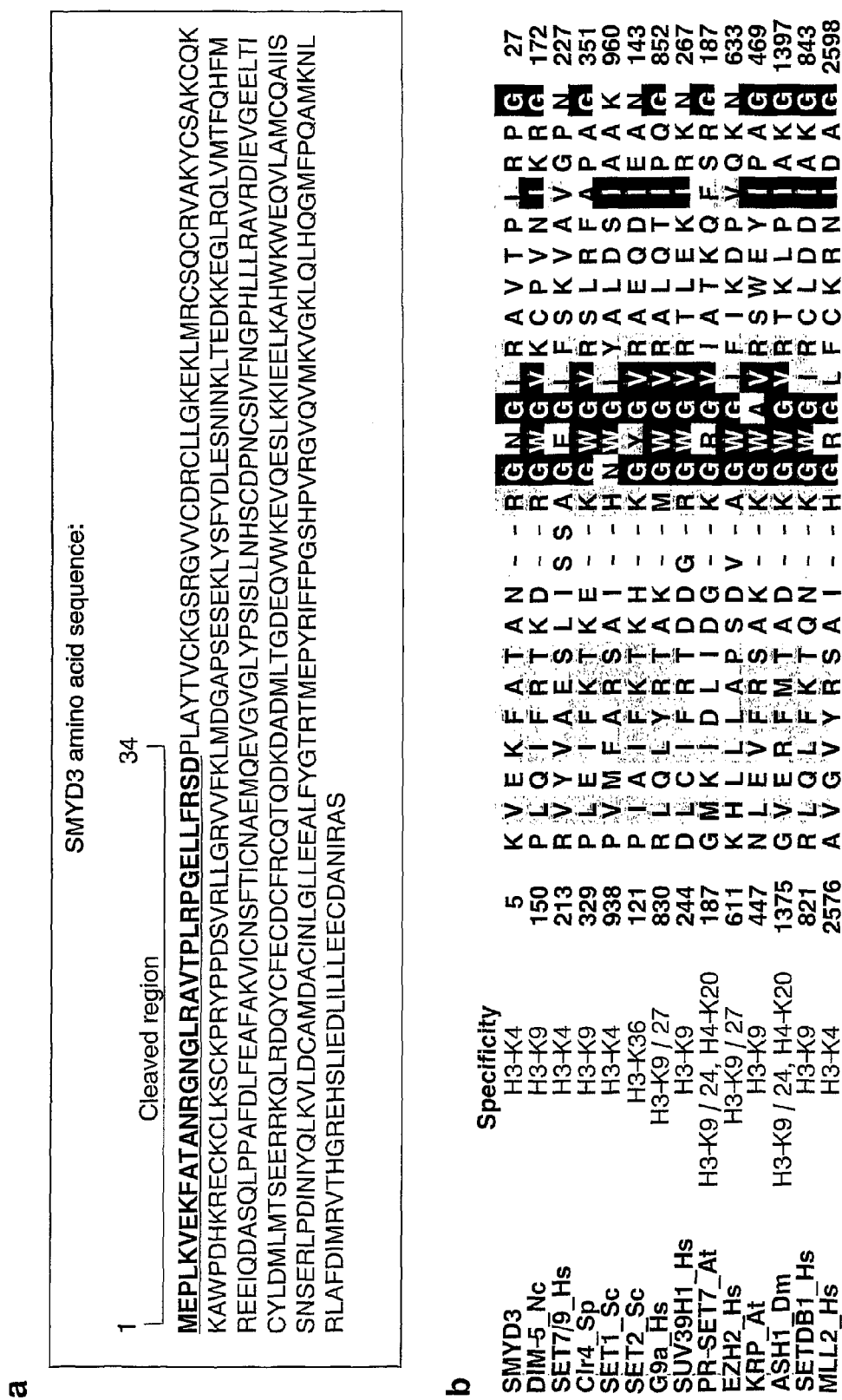
FIG. 9 Determination of SMYD3 cleavage site and conserved amino acid sequences of SET-N region in SET containing protein. Part a (SEQ ID NO: 2) depicts Edman amino acid sequence determined a 34 amino-acid-deleted SMYD3 protein in its N-terminal region. Part b (SEQ ID NOS:15-28) depicts alignment of amino acid sequences of SET-N in histone methyltransferases. Highly conserved amino acids were indicated in black boxes and moderately conserved amino acids were in shadowed boxes.

In an attempt to determine the exact cleavage site of SMYD3, we purified the 42-kDa protein from PVDF-membrane transferred with immunoprecipitated FLAG-tagged SMYD3 protein (FIG. 8b), and determined its amino acid sequence. As a result, we identified a deleted form of SMYD3 protein lacking N-terminal 34-amino acids, which revealed a cleavage site between codon 34 (aspartic acid) and codon 35 (proline) (FIG. 9a). SMYD3 contains an amino acid sequence termed SET-N region between codons 5 and 27, which is conserved in SET domain proteins (Marmorstein, R. Trends in Biochem. Sci., Vol. 8 no. 2, (2003); Kouzarides, T. Curr. Opin. Genet. Dev. 12, 198-209 (2002); Lachner, M and Jenuwein, T. Curr. Opin. Cell biol. 14, 286-298 (2002)). An alignment of amino acid sequences of SET-N region depicted the high similarity of the region in SMYD3 and other methyltransferases (FIG. 9b), implying the importance of this region.

Example 8

Figure 10:
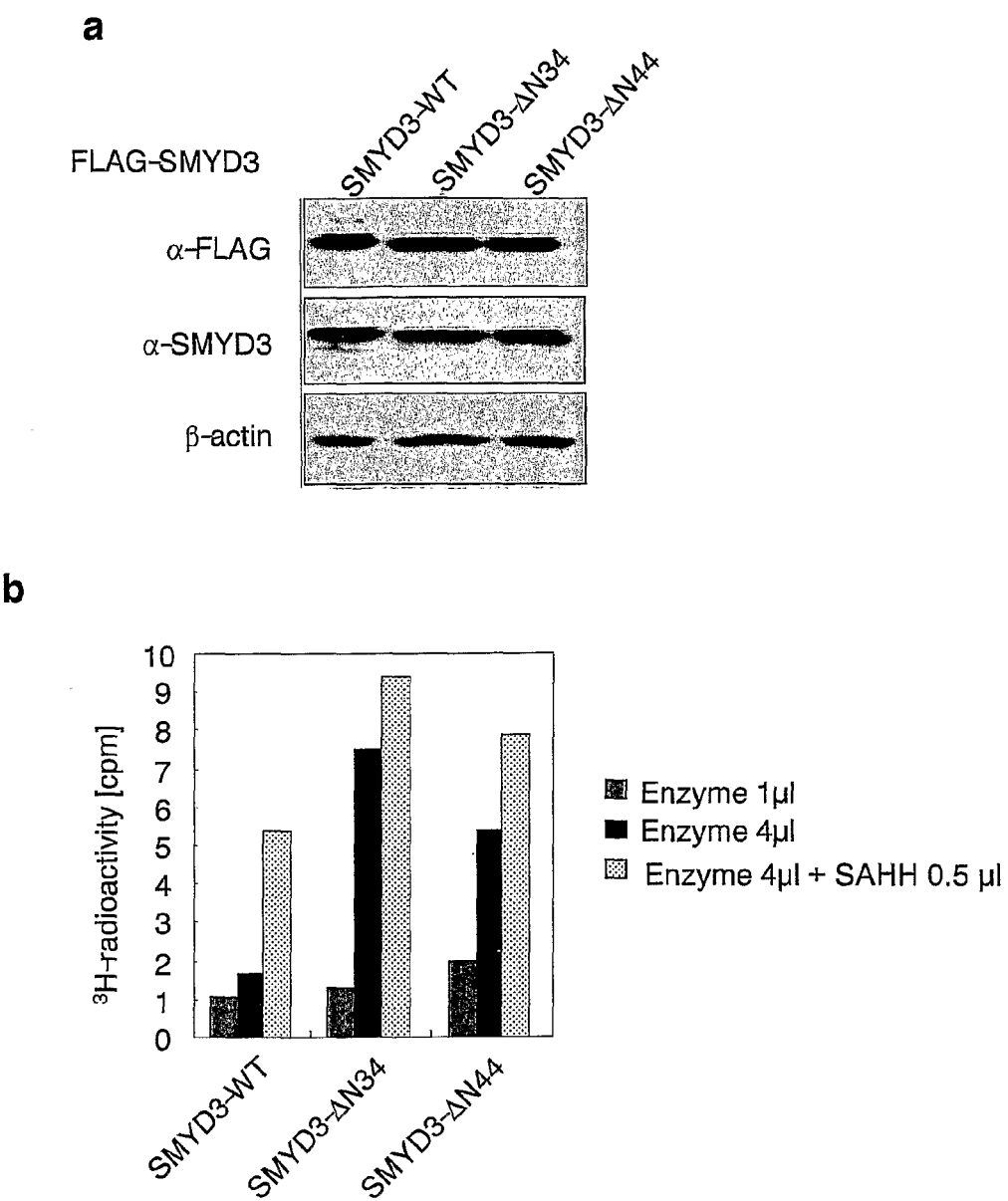
FIG. 10 Increased HMTase activity of the cleaved form of SMYD3 compared with the wild type protein. Part a depicts western blot analysis of wild-type or deleted forms (ΔN34 and ΔN44) of SMYD3 proteins with anti-FLAG antibody (upper panel) and anti-SMYD3 antibody (middle panel). Proteins were extracted from cells expressing FLAG-tagged SMYD3 proteins. Immunoprecipitated SMYD3 protein was used for an HMTase assay. Part b depicts dose-response increase of HMTase activity of the full-length and cleaved SMYD3 proteins. Addition of SAHH (S-adenosyl homocysteine hydrolase) increased the activity. 3H-radioactivity was measured by liquid scintillation counter.

Increased HMTase Activity of the Cleaved SMYD3 Compared with the Wild Type Protein To investigate the methyltransferase activity of the cleaved SMYD3 protein, we expressed 3×FLAG-tagged wild-type, or 34- or 44-amino acids-deleted forms of SMYD3 exogenously in HEK293 cells, and immunoprecipitated these proteins (FIG. 10a). We carried out a histone methyltransferase (HMTase) assay using these proteins as an enzyme source, and showed that HMTase activity of the wild-type SMYD3 increased in a dose-dependent manner (FIG. 10b). Reaction of methylation in the presence of a methyl donor, S-adenosyl methionine (SAM), accompanies production of S-adenosyl homocysteine (SAH), which may inhibit the methyltransferase reaction in a competitive manner. Therefore we added, in the reaction mixture, S-adenosyl homocysteine hydrolase (SAHH) that hydrolyzes SAH to homocysteine and adenosine. As expected, we observed striking increase of HMT activity in the presence of SAHH compared to its absence (FIG. 10b). This finding is useful for the screening of methyltransferase inhibitor(s) of SMYD3. Surprisingly, the cleaved SMYD3 proteins had significantly higher HMTase activity compared to the full-length protein (FIG. 10b). This result indicates that post-translational cleavage is involved in the regulation of SMYD3 HMTase activity in human cells, and that the N-terminal SET-N region may have a suppressive role for the HMTase activity Example 9

Glycine 15 and 17 in the SET-N Region is Important for the HMT Activity

Figure 11:
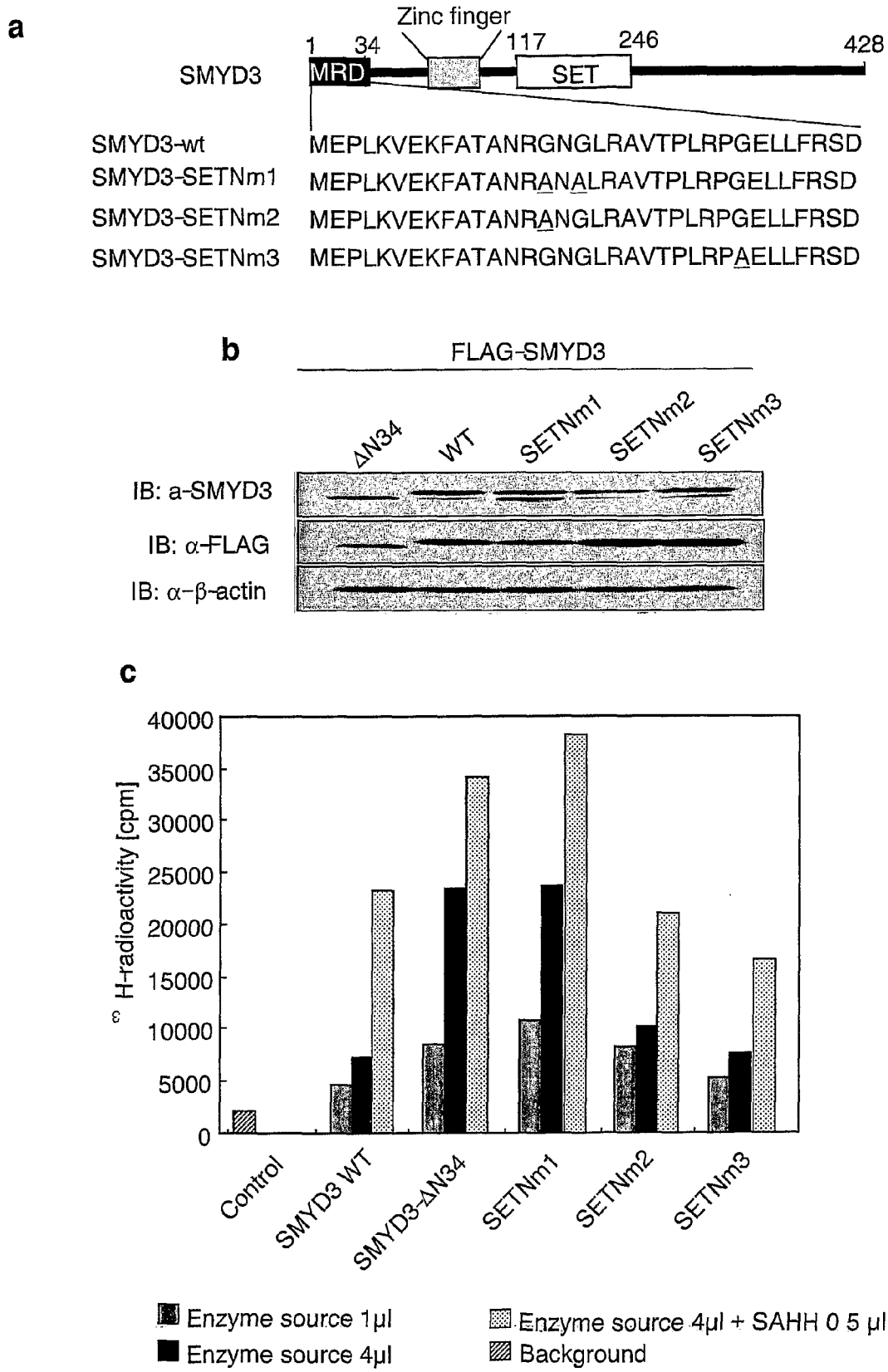
FIG. 11 Determination of responsible region for the suppressed HMTase activity in the SET-N region. Part a (SEQ ID NOS:34-37) depicts schematic presentation of mutated SMYD3 constructs containing substitution in the conserved amino acids of the SET-N region. Part b depicts immunoblot analysis of FLAG-tagged wild-type or mutant (ΔN34, SETNm1, SETNm2, and SETNm3) SMYD3 proteins with anti-SMYD3 (upper panel) or anti-FLAG (middle panel) antibody. Immunoprecipitated protein with anti-Flag antibody from HEK293F cells expressing FLAG-tagged SMYD3 was used as enzyme source for HMTase assay. Part c depicts HMTase activity of the wild-type, deleted forms of SMYD3. 3H-radioactivity was measured by liquid scintillation counter.

To determine the importance of the conserved amino acid sequence in the SET-N region for the suppressed enzyme activity, we prepared plasmids expressing wild-type or mutant N-terminal FLAG-tagged SMYD3 protein, SMYD3-SETNm1, -SETNm2, or -SETNm3, containing substitution(s) of both Gly15Ala and Gly17Ala, Gly15Ala, or Gly27Ala, respectively (FIG. 11a). Western blot of the lysates from HEK293 cells expressing these mutants showed that the substitutions did not affect the cleavage of SMYD3 protein (FIG. 11b, upper panel). We performed HMTase assay using immunoprecipitated SMYD3 protein. As a result, mutant proteins containing either Gly15Ala or Gly27Ala (SMYD3-SETNm2 or -SETNm3) had similar HMTase activity to wild-type protein (FIG. 11c). Whereas a mutant protein containing two substitutions of Gly15Ala and Gly17Ala (SMYD3-SETNm1) showed significantly enhanced activity compared to the wild-type protein (FIG. 11c). These data suggest that glycines 15 and 17 may play an important role for the regulation of HMTase activity of SMYD3.

Example 10

Figure 12:
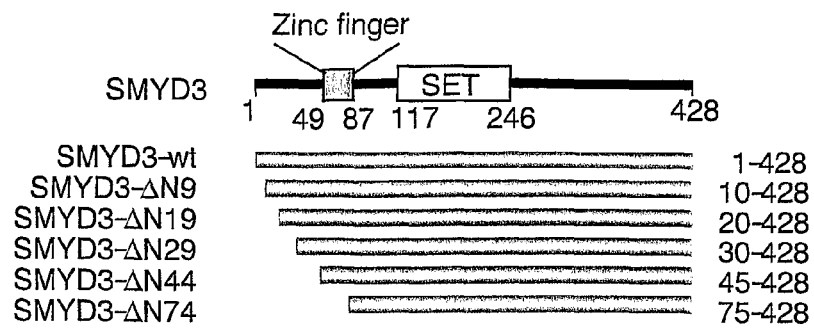
FIG. 12 Enhanced HMTase activity by the deletion of N-terminal region in SMYD3. Part a depicts Schematic presentation of deleted forms of SMYD3 in its N-terminal region. Plasmids expressing a series of GST-fused SMYD3 proteins were prepared. Part b depicts immunoblot analysis of recombinant SMYD3 proteins with anti-GST antibody. Wild-type and mutant recombinant SMYD3 proteins fused with GST were expressed in bacterial cells, and purified from the cells. Part c depicts in vitro HMTase activity of the proteins. 3H-radioactivity was measured by liquid scintillation counter.
Figure 12:
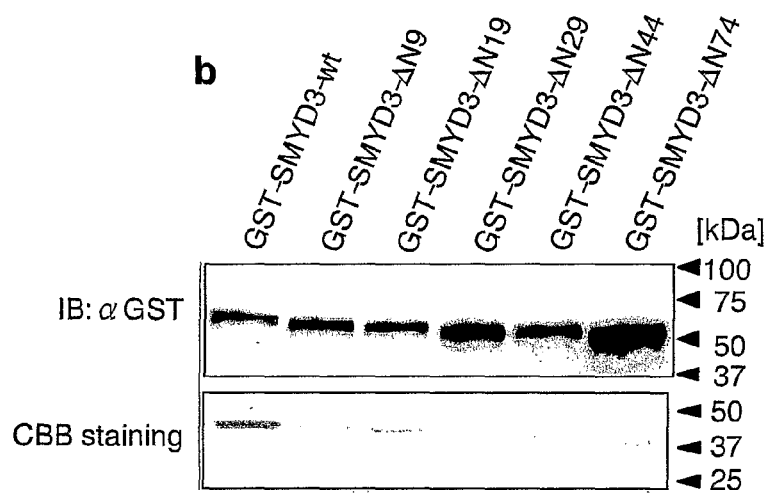
Figure 12:
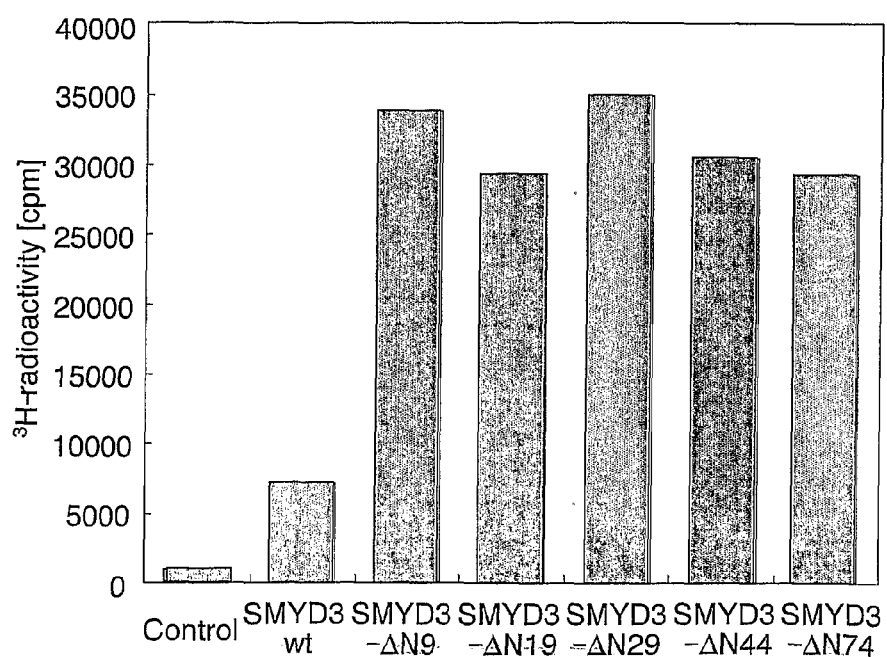

Deletion of N-Terminal 10 Amino Acids is Critical for the Enhanced HMTase Activity Since the N-terminal region enhanced its enzymatic activity, we hypothesized two possible mechanisms; the N-terminal region might associate with undetermined negative regulatory factor(s) for the enzyme activity, or the deletion might confer conformational change of the protein leading to enhanced enzyme activity. To determine whether additional negative regulatory factor(s) may play a role in the enzyme activity, we prepared recombinant proteins of wild-type and N-terminal deleted SMYD3, and investigated their HMTase activity in vitro. As shown in FIG. 12, all deletions mutants (SMYD3-ΔN9, -ΔN19, -ΔN29, -ΔN44, -ΔN74) exhibited four to five fold enhanced methyltransferase activity compared to the wild-type protein (FIG. 12). This result suggests that additional factor is not likely to be involved in the elevated activity of the cleaved SMYD3, and that the N-terminal ten-amino-acids may play a crucial role for the suppression of methyltransferase activity.

DISCUSSION

Disclosed herein is the finding that SMYD3 has a methyltransferase activity on lysine 824 of RB1 in vitro and in vivo, and that the methylated RB1 is more susceptible for phosphorylation by CDK/cyclin complex than unmethylated RB1. Consequently, HEK293-SMYD3 cells expressing SMYD3 showed elevated E2F-transcriptional activity compared to HEK293-Mock cells, which is in good agreement with growth-promoting effect of SMYD3, because E2F-1 overexpression can promoter transition from the G1 phase to the S phase of the cell cycle by regulating a series of genes whose products are essential for cell proliferation. Harbour et al. presented a model of RB1 phosphorylation during the G1-S progression, in which phosphorylation of RB1 initiates sequential intramolecular interaction between the C-terminal region and the pocket domain (Harbour, J. W. et al., D. C. Cell 98, 859-69 (1999)). During the G1 phase, phosphorylation of the C-terminal region of RB1 by CDK4/6-cyclin D triggers intramolecular interaction with the central pocket domain, which inhibits HDAC binding, thereby blocking active transcriptional repression. The interaction facilitates accession of CDK2/cyclin E to serine 567 of RB1, which, in turn, results in disruption of the A/B interface and preventing the RB1 interaction with E2F. In this model, successive phosphorylation of RB1 by both CDK4/6-cyclinD and CDK2/cyclin E complexes is required for the dissociation of E2F (Lundberg, A. S. & Weinberg, R. A. Mol Cell Biol 18, 753-61 (1998)). Reportedly, phosphorylation of Thr821 and Thr826 in RB1 inactivates the interaction between the A/B pocket domain and LXCXE motif-containing proteins including E2Fs and HDACs, while phosphorylation of Ser807 and Ser811 inactivates the C-terminal domain. This data agrees with the instant discovery that cells expressing SMYD3 show higher E2F transcriptional activity, as methylation of RB1 by SMYD3 enhanced the phosphorylation by CDK2/cyclin E or CDK6/cyclin D complexes, and phosphorylation of Thr821/826 is elevated. Alternatively, methylation of lysine 824 may directly change the conformation of the C-terminal region, and thereby inhibit the association of the pocket domain with E2F, because lysine methylation of both histones and p53 leads to their conformational change (Tsuge, M. et al. Nat Genet 37, 1104-7 (2005)). Since SMYD3 increases the transcriptional activity of E2F, elevated SMYD3 may enhance E2F1 activity as a positive feedback mechanism. Hence SMYD3-mediated RB1 inactivation is likely to play a crucial role in human carcinogenesis.

It is of note that RB1 plays a role in transcriptional repression through several mechanisms; RB1 interacts with transcription factors and directly suppresses their activity; recruitment of RB1 into the promoter region blocks the assembly of pre-initiation complexes; it also associates with class I HDACs (HDAC-1, -2, and -3), and induces the deacetylation of histones, resulting in conformational change to heterochromatin state; it forms a complex with DNMT1 leading to the DNA methylation in promoter region of target genes (Harbour, J. W. & Dean, D. C. Genes Dev 14, 2393-409 (2000); Robertson, K. D. et al. Nat Genet 25, 338-42 (2000)). In addition to these mechanisms, recent studies on histone methylation disclosed that RB1 also associates with histone methyltransferases including SUV39H, and Suv4-20h1 or Suv4-20h1, which are involved in H3-K9 and H4-K20 methylation, respectively (Gonzalo, S. et al. Nat Cell Biol 7, 420-8 (2005); Nielsen, S. J. et al. Nature 412, 561-5 (2001)). Bound to these methyltransferases, RB1 stabilizes heterochromatin formation by recruiting HP1 or CBX into the complex. The instant findings bring a novel insight into the regulation of transcriptional activation of histone H3-K4 methyltransferase. Methylated RB1 at lysine 824 enhances phosphorylation of RB1 and subsequent transactivation of E2F1 by presumably releasing it from the central pocket domain. In addition, methylated RB1 may change its conformation and thereby dissociate HDACs, heterochromatin protein 1 (HP 1), and/or chromobox proteins (CBXs) from the complex of SUV39H and/or Suv4-20h1 methyltransferases, leading to the reduced methylation of H3-K9 and H4-K20.

Although further investigation is warranted, the data herein highlight the importance of methylation of RB1 in the regulation of E2F responsible genes. Since RB1 binds to different methyltransferases, position and degree of methylation in RB1 may differ by the methyltransferases. Taken together that RB1 is also phosphorylated at different residues, the data herein suggest that a combination of multiple modifications in RB1 may define its biological properties, which is reminiscent of modification of histones and p53.

Mutation of RB1 is involved in not only sporadic and familial cases of retinoblastoma (Weinberg, R. A. Science 254, 1138-46 (1991)), but also other human cancers (Classon, M. & Harlow, E. Nat Rev Cancer 2, 910-7 (2002)). Several oncogenic viral proteins such as adenovirus E1A, HPV-E7, and simian virus 40 (SV40) large T antigen associate with RB1 in some types of cancers, which inhibits the interaction between RB1 and E2F leading to dissociation of E2F (Chellappan, S. P., et al. Cell 65, 1053-61 (1991); Bagchi, S., et al. Cell 65, 1063-72 (1991)). p16, an inhibitor of cyclin-dependent kinase 4, is frequently inactivated by methylation of its promoter, resulting in enhanced phosphorylation of RB1 by CDK/cyclin complexes in cancer cells (Nuovo, G. J., et al. Proc Natl Acad Sci USA 96, 12754-9 (1999)). These defects are reported to be involved in a part of colorectal and hepatocellular carcinomas (Chaubert, P. et al. Hepatology 25, 1376-81 (1997); Toyota, M. et al. Proc Natl Acad Sci USA 96, 8681-6 (1999)), and may not account for all cases in these types of tumors. Herein, a novel mechanism for inactivation of RB1 is disclosed, namely one that is caused by the methylation and subsequent enhanced phosphorylation of RB1. Since expression of SMYD3 is enhanced in the majority of colorectal and hepatocellular carcinomas, SMYD3 may play a crucial role in the proliferation of cancer cells by transactivation of E2F through abrogated RB1 tumor suppressor function. Interestingly, the present inventors recently discovered that SMYD3 expression is regulated by E2F-1 through its interaction to an E2F-1 binding element in the promoter region of SMYD3, and that the element comprises of two- or three-tandem repeats of E2F-1 binding motif. Allele frequency of the three-repeats in Japanese colorectal (n=350), liver (n=360), and breast (n=334) cancer patients was significantly higher than that in healthy controls (n=730) from general Japanese population. This data suggests that once SMYD3 is activated, it enhances E2F transcriptional activity through the modification of RB1, and consequently up-regulates SMYD3 by a positive feedback. Therefore, people containing three-repeats of E2F-1 binding element are more susceptible for the inactivation of RB1 by SMYD3 than those containing two-repeats. Additionally, the inhibition of SMYD3 appears to be a promising therapeutic strategy for colorectal and liver cancers, as well as bladder and breast cancers, because it will block the positive feedback loop, thereby efficiently suppress the E2F-1-mediated mitogenic activity by phosphorylation of RB1.

Herein, it was revealed that methylation of RB1 by SMYD3 may accelerates cell cycle progression from G1 to S phase through the enhanced phosphorylation of RB1 by CDK/cyclin complexes. This data indicates that methylation of lysine is important for not only histones but also other non-histone proteins, such as p53 and RB1. In addition, our findings have shed light on the novel mechanism of RB1 regulation that is involved in human carcinogenesis.

It has been shown that perturbation of epigenetic regulation is associated with human carcinogenesis. In addition to the abnormal DNA methylation in the promoter region of genes regulating cell cycle, DNA repair, and cell adhesion, recent investigations disclosed that histone methylation is also abrogated in human carcinogenesis. Histone methylation plays a crucial role in the regulation of gene expression through the change of chromatin structure. We reported that SMYD3, a histone H3-Lysine 4-specific methyltransferase, is over-expressed in several human cancers including HCC, CRC and breast carcinoma (Hamamoto, R. et al. Nat Cell Biol 6, 731-740 (2004): Hamamoto, R. et al. Cancer Sci 97, 113-118 (2006)). In our previous paper, we showed that its expression is elevated by transcriptional activation of E2F1, a transcription factor that is frequently enhanced in a variety of human cancer.

Protein function is regulated not only at post-transcriptional levels, but also by posttranslational modifications, which include cleavage of protein and other wide known modifications such as acetylation, phosphorylation, methylation, glycosylation and ubiquitination. These modifications are associated with protein stability, conformation of protein, and/or protein-protein interactions resulting in activation or inactivation of the protein. We have found that cleavage of SMYD3 increases its HMTase activity, which is reminiscent of regulation of critical enzymes such as pepsin, insulin, caspases, PARP, and MMPs, since cleavage of these proteins increases their enzymatic activity. This finding additionally suggests that an undetermined mechanism of the cleavage of SMYD3 may play a role in the modulation of HMTase activity. Therefore identification of the protease responsible for the cleavage, and clarification of the regulatory mechanism(s) will contribute to the development of novel therapeutic approaches to suppress SMYD3 activity. Furthermore a cleaved form of SMYD3 may be useful for the screening of SMYD3 inhibitors compared to full-length protein.

We have found in this study that loss of SMYD3 N-terminal region enhances its enzyme activity in vitro, suggesting that the deletion might confer conformational change of SMYD3 leading to the enhanced enzyme activity. Interestingly, HSP90 binds to N-terminal region of SMYD3 resulting in an increase of its HMTase activity. This data is in good agreement with the view that conformational change is involved in the HMTase activity, because HSP90 exerts a chaperone-like function contributing to stabilizing normal protein structure. Our findings also underscore the importance of the conserved SET-N region for regulation of HMTase activity. This conserved region may also act as a negative regulator of HMTases in other SET domain containing proteins. Further studies will uncover the mechanisms of regulation of HMTase activity in SET domain containing proteins.

We have shown here that an N-terminal cleaved form of SMYD3 protein is expressed in cancer cells and that the cleaved protein has markedly higher HMTase activity than full-length protein. These data implied that a post-translational regulatory system regulates the HMTase activity through a possible conformational change of the protein. Furthermore, we have found that an addition of SAHH increases the methyltransferase activity of SMYD3. Our findings will help for the better understanding of the regulatory mechanisms of SMYD3 activity, and may contribute to the identification of novel therapeutic strategies to inhibit the HMTase activity.

INDUSTRIAL APPLICABILITY

The methods described herein are useful in the identification of additional molecular targets for prevention, diagnosis and treatment of various cancers, including colorectal cancer, hepatocellular cancer, breast cancer and bladder cancer. Furthermore, the data reported herein add to a comprehensive understanding of cancer, facilitate development of novel diagnostic strategies, and provide clues for identification of molecular targets for therapeutic drugs and preventative agents. Such information contributes to a more profound understanding of tumorigenesis, and provides indicators for developing novel strategies for diagnosis, treatment, and ultimately prevention of cancer. While the present invention has been described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention. Thus, the invention is intended to be defined not by the above description, but by the following claims and their equivalents.

The invention claimed is

1. A method for identifying an agent that modulates methylation of a retinoblastoma peptide by SMYD3, said method comprising the steps of:
   a. contacting an SMYD3 polypeptide having a methyltransferase activity selected from the group consisting of:
   i. a polypeptide comprising the amino acid sequence of SEQ ID NO: 2;
   ii. a polypeptide that comprises the amino acid sequence of positions 117 to 246 of the amino acid sequence of SEQ ID NO: 2, wherein said polypeptide has a methyltransferase activity equivalent to the polypeptide consisting of the amino acid sequence of SEQ ID NO:2;
   iii. a polypeptide that comprises the amino acid sequence of positions 1 to 250 of the amino acid sequence of SEQ ID NO: 2;
   iv. a polypeptide that comprises the amino acid sequence of positions 45 to 428 of the amino acid sequence of SEQ ID NO: 2;
   v. a polypeptide that comprises the amino acid sequence of SEQ ID NO: 2 in which the amino acids of positions 1 to 30 have been deleted;
   vi. a polypeptide that comprises the amino acid sequence of SEQ ID NO: 2 in which the amino acids of positions 1 to 44 are deleted;
   vii. a polypeptide that comprises the amino acid sequence of SEQ ID NO: 2 in which the amino acids of positions 1 to 20 are deleted; and
   viii. a polypeptide that comprises the amino acid sequence of SEQ ID NO: 2 in which the amino acids of positions 1 to 10 are deleted;
   with the retinoblastoma peptide to be methylated and a cofactor in the presence of the agent under conditions suitable for methylation of the retinoblastoma peptide;
   b. detecting the methylation level of the retinoblastoma peptide; and
   c. comparing the methylation level of step (b) with a control level detected in the absence of the agent,
   wherein an increase or decrease in the methylation level compared to the control level indicates that the agent modulates the methylation of the retinoblastoma peptide by SMYD3.

2. The method of claim 1, wherein the retinoblastoma peptide comprises the amino acid sequence of SEQ ID NO: 4, or is a functional mutant comprising the amino acid sequence of SEQ ID NO: 4, including one or more of the following mutations: K889A, K896A, K791A, K814A, K791A and K824A, and K814A and K824A or is a functional fragment consisting of the amino acid sequence of positions 769-921 of the amino acid sequence of SEQ ID NO: 4.

3. The method of claim 1, wherein said cofactor is S-adenosyl homocysteine hydrolase (SAHH).

* * * * *